(12) United States Patent
Kaachra et al.

(10) Patent No.: US 10,808,259 B2
(45) Date of Patent: Oct. 20, 2020

(54) EXPRESSION CONSTRUCT AND PROCESS FOR ENHANCING THE CARBON, NITROGEN, BIOMASS AND YIELD OF PLANTS

(75) Inventors: Anish Kaachra, Palampur (IN); Surender Kumar Vats, Palampur (IN); Paramvir Singh Ahuja, Palampur (IN); Sanjay Kumar, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 213 days.

(21) Appl. No.: 14/112,681

(22) PCT Filed: Apr. 19, 2012

(86) PCT No.: PCT/IB2012/051965
§ 371 (c)(1),
(2), (4) Date: Jan. 27, 2014

(87) PCT Pub. No.: WO2012/143877
PCT Pub. Date: Oct. 26, 2012

(65) Prior Publication Data
US 2014/0137297 A1 May 15, 2014

(30) Foreign Application Priority Data
Apr. 19, 2011 (IN) .......................... 1143/DEL/2011

(51) Int. Cl.
*C12N 15/82* (2006.01)

(52) U.S. Cl.
CPC ..... *C12N 15/8243* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 8,541,208 B1 | 9/2013 | Plesch et al. | |
| 2002/0069430 A1* | 6/2002 | Kisaka | C12N 9/0004 800/290 |
| 2006/0127889 A1* | 6/2006 | Dotson | C12Q 1/6851 435/6.12 |
| 2007/0118916 A1 | 5/2007 | Puzio et al. | |
| 2007/0271623 A1* | 11/2007 | Andreasson | C07K 14/415 800/265 |

FOREIGN PATENT DOCUMENTS

| | | | | |
|---|---|---|---|---|
| CA | 2644273 | | 3/2008 | |
| EP | 2090662 | * | 8/2009 | ............ C12N 15/82 |
| WO | WO 2008034648 A1 | * | 3/2008 | ......... C12N 15/8218 |
| WO | WO 2009037329 A2 | * | 3/2009 | ......... C12N 15/8261 |
| WO | WO 2010034681 A1 | * | 4/2010 | ............ C07K 14/415 |

OTHER PUBLICATIONS

Sirchia et al. (Promega Scientific Style and Format, 7th edition, 2006).*
Roberts et al. (Genbank Accession AF234298.1).*
Kumar et al. (Photosynthesis Research (2006) 88: 63-71).*
Cheng et al. (Plant Physiol. (1997) 115: 971-980).*
Kumar et al. (Photosynthetica 46 (4): 611-614, 2008). (Year: 2008).*
Temple, S., et al., (1998) "Glutamate synthase and nitrogen assimilation", Trends in Plant Science, 3(2):51-56.
Good, A G, et al., (2004) "Can less yield more? Is reducing nutrient input into the environment compatible with maintaining crop production?", Trends in Plant Science, 9(12):597-605.
Cai et al., Overexpressed glutamine synthetase gene modifies nitrogen metabolism and abiotic stress responses in rice, Plant Cell Rep (2009) 28:527-537.
Chen et al., Overexpression of a cyanobacterial phosphoenolpyruvate carboxylase with diminished sensitivity to feedback inhibition in *Arabidopsis* changes amino acid metabolism, Planta (2004) 219: 440-449.
Fuentes et al., "Over-expression of cytosolic glutamine synthetase increases photosynthesis and growth at low nitrogen concentrations", Journal of Experimental Botany, vol. 52, No. 358, pp. 1071-1081, May 2001.
Fukayama et al., "Activity regulation and physiological impacts of maize $C_4$-specific phosphoenolpyruvate carboxylase overproduced in transgenic rice plants", Photosynthesis Research 77: 227-239, 2003.
Hudspeth et al., "Expression of Maize Phosphoenolpyruvate Carboxylase in Transgenic Tobacco$_1$", Plant Physiol. (1992) 98, 458-464.
Ku et al., "High-level expression of maize phosphoenolpyruvate carboxylase in transgenic rice plants", Nature Biotechnology, vol. 17, Jan. 1999.
Lebouteiller et al., Physiological impacts of modulating phosphoenolpyruvate carboxylase levels in leaves and seeds of *Arabidopsis thaliana*, Plant Science, 172 (2007) 265-272.
Murooka et al., Variation of the Amino Acid Content of *Arabidopsis* Seeds by Expressing Soybean Aspartate Aminotransferase Gene, Journal of Bioscience and Bioengineering, vol. 94, No. 3, 225-230, 2002.
Oliveira et al., "Overexpression of Cytosolic Glutamine Synthetase Relation to Nitrogen, Light, and Photorespiration", Plant Physiology, Jul. 2002, vol. 129, pp. 1170-1180.
Sentoku et al., Analysis of the transgenic tobacco plants expressing Panicum miliaceum aspartate aminotransferase genes, Plant Cell Reports (2000) 19: 598-603.
Takahashi et al., Pleiotrophic Modulation of Carbon and Nitrogen Metabolism in *Arabidopsis* Plants Overexpressing the NAD kinase2 Gene$^1$[$^W$], Plant Physiology®, Sep. 2009, vol. 151, pp. 100-113.

(Continued)

*Primary Examiner* — Charles Logsdon
(74) *Attorney, Agent, or Firm* — Blank Rome LLP

(57) ABSTRACT

The assimilated C and N largely influence plant growth and crop yields. Previous attempts to alter the carbon and nitrogen status of the plants attempted with one or two genes The present invention involves simultaneous co-overexpression of three genes wherein one gene (PEPCase) efficiently capture CO2 whereas the other two encode for enzymes (Asp AT and GS) involved in nitrogen assimilation. The combined effect is the enhancement of carbon and nitrogen status of the plant and the productivity.

7 Claims, 7 Drawing Sheets
Specification includes a Sequence Listing.

(56) References Cited

OTHER PUBLICATIONS

Vincent et al., "Overexpression of a soybean gene encoding cytosolic glutamine synthetase in shoots of transgenic *Lotus corniculatus* L. plants triggers changes in ammonium assimilation and plant development", Planta (1997) 201: 424-433.
Yanagisawa et al., Metabolic engineering with Dof1 transcription factor in plants: Improved nitrogen assimilation and growth under low-nitrogen conditions, PNAS, May 2004, vol. 101, No. 20, pp. 7833-7838.
Zhou et al., Over-expression of aspartate aminotransferase genes in rice resulted in altered nitrogen metabolism and increased amino acid content in seeds, Theor Appl Genet (2009) 118:1381-1390.

\* cited by examiner a b

Leaves                                        Roots

EXPRESSION CONSTRUCT AND PROCESS FOR ENHANCING THE CARBON, NITROGEN, BIOMASS AND YIELD OF PLANTS

The following specification particularly describes the invention and the manner in which it is to be performed:

FIELD OF THE INVENTION

The present invention relates to an expression construct for enhancing the carbon (C), nitrogen (N), biomass and yield of plants.

Further, the present invention provides the process for enhancement of C and N levels and subsequent improvement in the biomass and yield of plant by using the aforesaid expression construct which utilizes co-overexpression of genes from enzymes phosphoenolpyruvate carboxylase (hereinafter, referred as "PEPCase"), glutamine synthetase (hereinafter, referred as "GS") and aspartate aminotransferase (hereinafter, referred as "AspAT"). In particular, the present invention is directed to transgenic plants where nucleic acid sequences encoding the said proteins are expressed in plant cells. More particularly, the present invention relates to the transformation of a plant with genetic construct involving co-overexpression of three genes wherein one gene PEPCase encodes enzyme responsible to capture $CO_2$ and the other two encode for enzymes (AspAT and GS) involved in N assimilation wherein the N assimilation requires C skeleton which is met by PEPCase, under the control of constitutive promoter comprising plant *Arabidopsis thaliana* transformed with AspAT+GS+PEPCase gene and expression of this gene in plants, thereby enhancing the status of C and N, biomass and yield of plant.

BACKGROUND OF THE INVENTION AND PRIOR ART

The present invention relates to a transformed plant with co-overexpression of three genes, viz.

AspAT, GS and PEPCase, leading to enhanced C, N content, biomass, and yield component. PEPCase (EC. 4.1.1.31) is a ubiquitous enzyme in plants that catalyses the β-carboxylation of phosphoenolpyruvate (hereinafter, referred as "PEP") in the presence of $HCO_3^-$ and $Mg_2^+$ to yield oxaloacetate (hereinafter, referred as "OAA") and inorganic phosphate (hereinafter, referred as "Pi"), and it primarily has an anaplerotic function of replenishing the tricarboxylic acid cycle with intermediates. In higher plants, there are several isoforms of PEPCase of different organ specificities and they are involved in a variety of functions including stomata opening, fruit ripening and seed maturation. The leaves of C4 and CAM plants contain high levels of PEPCase, which catalyze the initial $CO_2$ fixation of photosynthesis. The much lower levels of PEPCase seen in the leaves of C3 plants contribute to an anaplerotic function and play a role in regulation of the cellular pH.

GS (EC 6.3.1.2) catalyses the ATP-dependent condensation of ammonia (hereinafter, referred as "$NH_3$") with glutamate (hereinafter, referred as "Glu") to produce glutamine (hereinafter, referred as "Gln"). Subsequently, glutamate synthase (GOGAT) transfers the amide group of Gln to α-ketoglutarate producing two molecules of Glu. Both Gln and Glu are the primary source of organic N for proteins, nucleic acid and chlorophyll.

AspAT (EC 2.6.1.1) catalyzes the reversible transfer of the amino group of asparate (hereinafter, referred as "Asp") to α-ketoglutarate to form OAA and Glu. In plants, AspAT has been proposed to play several metabolic roles including: recycling of C skeletons during $NH_3^+$ assimilation in roots, providing amide precursors for biosynthesis of major nitrogen transport molecules such as asparagines (hereinafter, referred as "Asn") and ureides, recruiting Asn nitrogen during seed filling and participating in intracellular C shuttles in C4 plants providing precursors for the biosynthesis of the Asp family of amino acids.

Plant performance in terms of biomass production, yield or harvest index depends upon number of internal and environmental factors. Among all these factors, plant C and N level is one of the important factors governing plant productivity. The emerging details of C and N assimilation suggest that a regulatory system coordinates the uptake and distribution of these nutrients in response to both metabolic and environmental cues. Plants sense changes in their C and N status and relay this information to the nucleus where changes in gene expression are brought about. Since plant growth and crop yield are largely influenced by the assimilated C and N, many attempts have been made in the past to engineer efficient C and N assimilation. However, there is no report yet which show significant improvement in the status of C, N, biomass and yield in plants.

Table 1 illustrates the status of information available on the various strategies to improve C and/or N and biomass in different plants.

TABLE 1

| Functions | Transformation System adopted | Results | Reference |
|---|---|---|---|
| NAD kinase2 (NADK2) Catalyzes the synthesis of NADP from NAD in chloroplasts | *Arabidopsis* NADK2 overexpressor and nadk2 mutant were studied to investigate the impact of altering NADP level on plant metabolism. | NADK2 overexpressors were characterized by increase in calvin cycle intermediates and amino acid like Glu and Gln. However, there is no clear evidence on role of NADK2 influencing C and N metabolism. | Takahashi, H., Takahara, K., Hashida, S., Hirabayashi, T., Fujimori, T., Yamada, M. K., Yamaya, T., Yanagisawa, S. and Uchimiy, H. 2009. Plant Physiol. 151: 100-113. |

TABLE 1-continued

| Functions | Transformation System adopted | Results | Reference |
|---|---|---|---|
| Dof 1<br>Dof1 is a transcription activator for multiple gene expressions associated with the organic acid metabolism, including PEPCase. | Maize Dof1 cDNA was overexpressed in *Arabidopsis* plants under derivative of the 35S promoter designated as 35SC4PPDK. | Dof1 overexpression in *Arabidopsis* has led to co-operative modification of plant C and N content, with improved growth under low N conditions. However, effect of CN alteration on plant biomass or yield was not discussed. | Yanagisawa, S., Akiyama, A., Kisaka, H., Uchimiya, H. and Miwa, T. 2004. Proc. Natl. Acad. Sci. USA. 101: 7833-7838 |
| GS<br>GS catalyses the ATP- dependent condensation of $NH_3$ with (Glu) to produce (Gln). | i.) A soybean cytosolic GS gene (GS15) fused with the constitutive CaMV 35S promoter in order to direct its over-expression in *Lotus corniculatus* L. plants. | Over expression of cytosolic GS accelerated plant development, leading to early senescence and premature flowering when grown $NH_4^+$ rich medium. Limitation of C skeleton and energy for enhanced $NH_4^+$ assimilation were anticipated. | Vincent, R., Fraisier, V., Chaillou, S., Limami, M. A., Deleens, E., Phillipson, B., Douat, C., Boutin, J.-P. and Hirel, B. 1997. Planta. 201: 424-433. |
| | ii.) A pea cytosolic GS gene was overexpressed in tobacco plants | Overexpression of cytosolic GS in relation to N, light and photorespiration suggested an alternative route to chloroplastic GS for assimilation of photorespiratory ammonium. | Oliveira, I.., Brears, T., Knight, T., Clark, A. and Coruzzi, G. 2002, Plant Physiol. 129: 1170-1180 |
| | iii.) Full-length cDNAs encoding rice cytosolic GS genes (OsGS1;1 and OsGS1;2) along with *E. coli* GS gene (glnA) were overexpressed in the rice plant under constitutive CaMV 35S promoter. | An increased metabolic level in GS-overexpressed plants was obtained, which showed higher total GS activities and soluble protein concentrations in leaves and higher total amino acids and total N content in the whole plant. However, decrease in both grain yield production and total amino acids were observed in seeds of GS-overexpressed plants compared with wild-type plants. | Cai, H., Zhou, Y., Xiao, J., Li, X., Zhang, Q. and Lian, X. 2009, Plant Cell Rep. 28: 527-537 |
| | iv) cDNA encoding alfa alfa cytosolic GS over expressed in tobacco plants | Transgenic plants grew better under N starvation by maintaining photosynthesis at rate comparable to those of plants under high N, while photosynthesis in control plants was inhibited by 40-50%. These results further reflect the need for cooperative modification of CN metabolism for developing plants with better agronomic traits. | Fuentes, S., Allen, D., Ortiz-Lopez, A. and Hernandez, G. 2001. J. Exp. Bot. 52: 1071-1081. |

TABLE 1-continued

| Functions | Transformation System adopted | Results | Reference |
|---|---|---|---|
| PEPCase PEPCase catalyses the β-carboxylation of PEP in the presence of $HCO_3^-$ and $Mg_2^+$ to yield OAA and Pi. | i) The intact maize gene encoding C4-specific PEPCase used for transformation of rice plants | Transgenic plants exhibited higher PEPCase activity with reduced $O_2$ inhibition of photosynthesis. It was found that the reduced $O_2$ inhibition photosynthesis was primarily due to reduction of Pi rather than increase in the partial direct fixation of atmospheric $CO_2$ via the enhanced maize PEPCase. However, no report on biomass accumulation or yield as a consequence of PEPCase overexpression was reported. | Agarie, S., Miura, A., Sumikura, R., Tsukamoto, S., Nose, A., Arima, S., Matsuoka, M. and Tokutomi, M. M. 2002. Plant Sci. 162: 257-265. |
| | ii) Maize PEPCase introduced in to tobacco plants under the control maize PEPCase and tobacco chlorophyll a/b binding protein gene promoter. | Higher levels of maize PEPCase transcript of the correct size were obtained using tobacco (chlorophyll a/b binding protein gene promoter. With two fold incerase in PEPCase activities in leaf, transgenic plants had significantly elevated levels of titratable acidity and malic acid. However, these biochemical differences did not produce any significant physiological changes with respect to photosynthetic rate or $CO_2$ compensation point. | Hudspeth, R. L., Grula, J. W., Dai, Z., Edwards, G. E. and Ku, M. S. B. 1992. Plant Physiol. 98: 458-464 |
| AspAT AspAT catalyzes the reversible transfer of the amino group of (Asp) to a-ketoglutarate to form OAA and Glu | i) *Panicum miliaceum* L. mitochondrial and cytosolic AspAT (mAspAT and cAspAT, respectively) genes were expressed in tobacco plants under CaMV 35S promoter. | mAspAT- or cAspAT-transformed plants had about threefold or 3.5-fold higher AspAT activity in the leaf than non-transformed plants, respectively. Leaves of both transformed plants had increased levels of PEPCase and transformed plants with cAspAT also had increased levels of mAspAT in the leaf. These results further suggested interaction between C and N metabolism. | Sentoku, N., Taniguchi, M., Sugiyama, T., Ishimaru, K., Ohsugi, R., Takaiwa, F. and Toki, S. 2000. Plant Cell Rep. 19: 598-603. |
| | ii) Three AspAT genes from rice (OsAAT3) and one AspAT gene from *E. coli* (EcAAT) were over expressed under CaMV 35S promoter in rice plants. | Compared with control plants, the transformants showed significantly increased leaf AspAT activity and greater seed amino acid and protein contents. However, influence of CN level on biomass or yield was not discussed. | Zhou. Y., Cai, H., Xiao, J. Li, X., Zhang, Q. and Lian, X. 2009. Theor Appl Genet. 118: 1381-1390 |

Higher activity of PEPCase shall facilate $CO_2$ capturing and makes the carbon backbone available for routing of nitrogen in to organic form through joint activity of AspAT and GS. As a result, the inventors have found that object of the present invention can be attained by concomitant increase in expression of genes encoding AspAT, GS and PEPCase to establish the present invention.

Below is given a state of the art knowledge in relation to the present invention and the attempts previously made to enhance either carbon and/or nitrogen levels in the plant. Reference may be made to article by Hudspeth, R. L., Grula, J. W., Dai, Z., Edwards, G. E. and Ku, M. S. B., entitled "Expression of miaze phosphoenolpyruvate carboxylase in transgenic tobacoo" (1992, Plant Physiology, 98: 458-464), wherein PEPCase from maize was expressed under a tobacco (Nicotiana plumbaginifolia) chlorophyll a/b binding protein gene promoter in tobacco plants. Up to two fold higher activity of PEPCase was observed in the transgenic leaves as compared to non-transformants with elevated levels of titratable acidity and malic acid. However, these biochemical differences did not produce any significant physiological changes with respect to photosynthetic rate or $CO_2$ compensation point.

Reference may be made to article by Lebouteiller, B., Dupont, A. G., Pierre, J. N., Bleton, J., Tchapla, A., Maucourt, M. and Moing, A., Rolin, D., and Vidal, J. entitled "Physiological impacts of modulating phosphoenolpyruvate carboxylase levels in leaves and seeds of Arabidopsis thaliana" (2007, Plant Science, 172:256-272,), wherein the PEPCase of sorghum was expressed under CaMV 35S promoter in Arabidopsis plant. The leaves of the primary transformants showed up to ten-fold increase in PEPCase activity and up to 30% increase in the dry weight and total protein content of seeds. However, the transformants (primary and progeny) did not show any improved growth phenotype or modification in seed production per plant Reference may be made to yet another article by Chen, L. M., Li, K. Z. Miwa, T. and Izui, K. entitled "Overexpression of a cyanobacterial phosphoenol pyruvate carboxylase with diminished sensitivity to feedback inhibition in Arabidopsis changes amino acid metabolism" (2004, Planta, 219: 440-419.), wherein the cyanobacterial Synechococcus vulcanus phosphoenolpyruvate carboxylase (SvPEPCase) with diminished sensitivity to feed back inhibition, was over expressed under the control of CaMV 35S promoter in Arabidopsis plant. One third of the $T_1$ transformants showed severe phenotypes as bleached leaves and were infertile when grown on soil. However, no such phenotype was observed with Arabidopsis transformed with maize PEPCase (ZmPEPC) for $C_4$ photosynthesis, which is normally sensitive to a feedback inhibitor, L-malate. The growth inhibition of SvPEPC transformed $T_2$ plants was presumed to be primarily due to a decreased availability of phosphoenolpyruvate (PEP), one of the precursors for the shikimate pathway for the synthesis of aromatic amino acids and phenylpropanoids.

Reference may be made to yet another article by Fukayama, H., Hatch, M. D., Tamai, T., Tsuchida, H., Sudoh, S., Furbank, R. T. and Miyao, M., entitled "Activity regulation and physiological impacts of maize C (4)-specific phosphoenolpyruvate carboxylase overproduced in transgenic rice plants" (2003, Photosynthesis Research, 77: 227-239), wherein the intact maize PEPCase gene was overexpressed in the leaves of rice plants. Introduced PEPCase in transgenic rice leaves underwent activity regulation through protein phosphorylation in manner similar to endogenous rice PEPCase but contrary to that occurring in maize leaves, being downregulated in the light and upregulated in the dark. Compared with untransformed rice, the level of PEP was slightly lower and the product (OAA) was slightly higher in transgenic rice, suggesting that maize PEPCase was functioning even though it remained dephosphorylated and less active in the light. $^{14}CO_2$ labeling experiments indicated that maize PEPCase did not contribute significantly to the photosynthetic $CO_2$ fixation of transgenic rice plants. Rather, it slightly lowered the $CO_2$ assimilation rate. This effect was ascribable to the stimulation of respiration in the light, which was more marked at lower O2 concentrations. It was concluded that overproduction of PEPCase does not directly affect photosynthesis significantly but it suppresses photosynthesis indirectly by stimulating respiration in the light.

Reference may be made to yet another article by Vincent, R., Fraisier, V., Chaillou, S., Limami, M. A., Deleens, E., Phillipson, B., Douat, C., Boutin, J. P. and Hirel, B., entitled "Overexpression of a soybean gene encoding cytosolic glutamine synthetase in shoots of transgenic Lotus corniculatus L. plants triggers changes in ammonium assimilation and plant development" (1997, Planta. 201:424-433), wherein a soyabean cytosolic GS gene GS15 was fused with CaMV 35S promoter to achieve constitutive expression in the lotus corniculatus L. plants. On growing the transgenic plants under different N regimes an increase in free amino acids and ammonium was observed accompanied by a decrease in soluble carbohydrates in the transgenic plants cultivated with 12 mM $NH^{4+}$ in comparison to the wild type grown under the same conditions. Labelling experiments revealed that both ammonium uptake in the roots and the subsequent translocation of amino acids to the shoots was lower in plants over expressing GS. However the early floral development in the transformed plants suggested the role of GS in the early senescence and premature flowering when plants were grown on an ammonium-rich medium. Limitation of C skeleton and energy for enhanced $NH_4^+$ assimilation were anticipated.

Reference may be made to yet another article by Fuentes, S. I., Allen, D. J., Ortiz-Lopez, A. and Hernandez, G., entitled "Overexpression of cytosolic glutamine synthetase increases photosynthesis and growth at low nitrogen conditions" (2001, Journal of Experimental Botany, 52:1071-1081), wherein the alfa alfa GS driven by constitutive CaMV 35S promoter introduced into tobacco plants. Leaf GS activity in the transgenic plants increased up to six times of untrasformed plants. Under N starvation GS transgenic grew better by maintenance of photosynthesis at rates indistinguishable from plants under high N, while photosynthesis in the control plants was inhibited by 40-50% by N deprivation. However, under optimum N fertilization conditions, no effect of GS overexpression on photosynthesis or growth was observed.

Reference may be made to yet another article by Oliveira, I., Brears, T., Knight, T., Clark, A. and Coruzzi, G., entitled "Overexpression of cytosolic glutamine synthetase. Relation to nitrogen, light, and photorespiration" (2002, Plant Physiology, 129: 1170-1180), wherein the overexpression of pea cytosolic GS was studied in relation to nitrogen, light and photorespiration. Tobacco plants, which ectopically overexpress cytosolic GS1 in leaves, display a light-dependent improved growth phenotype under N-limiting and N-nonlimiting conditions as evident by increase in fresh weight, dry weight, and leaf soluble protein. The cytosolic GS1 transgenic plants also exhibit an increase in the $CO_2$ photorespiratory burst and an increase in levels of photorespiratory intermediates, suggesting changes in photorespiration. However, the effect of stimulation of photorespiration by GS overexression on plant productivity was not discussed.

Reference may be made to yet another article by Cai, H., Zhou, Y., Xiao, J., Li, X., Zhang, Q. and Lian, X., entitled "Overexpressed glutamine synthetase gene modifies nitrogen metabolism and abiotic stress response in rice" (2009, Plant Cell Reports. 28: 527-537), wherein the full-length cDNAs encoding rice (*Oryza sativa*) cytosolic GS genes (OsGS1;1 and OsGS1;2) along with *E. coli* GS gene (glnA) were overexpressed in the rice plant under constitutive CaMV 35S promoter. An increased metabolic level in GS-overexpressed plants was obtained, which showed higher total GS activities and soluble protein concentrations in leaves and higher total amino acids and total N content in the whole plant. However, decrease in both grain yield production and total amino acids were observed in seeds of GS-overexpressed plants compared with wild-type plants.

Reference may be made to yet another article by Sentoku, N., Taniguchi, M., Sugiyama, T., Ishimaru, K., Ohsugi, R., Takaiwa, F. and Toki, S., entitled "Analysis of the transgenic tobacco plants expressing *Panicum miliaceum* aspartate aminotransferase genes" (2000, Plant Cell Reports, 19: 598-603), wherein the effects of the overexpression of *Panicum* mitochondrial and cytoplasmic AspAT (mAspAT and cAspAT respectively) under the control of CaMV 35S promoter were evaluated on transgenic tobacco plants. The mAspAT- or cAspAT-transformed plants had about threefold or 3.5-fold higher AspAT activity in the leaf than non-transformed plants, respectively. Interestingly, the leaves of both transformed plants had increased levels of PEPCase and transformed plants with cAspAT also had increased levels of mAspAT in the leaf. These results suggest that the increased expression of *Panicum* cAspAT in transgenic tobacco enhances the expression of its endogenous mAspAT and PEPCase, and the increased expression of *Panicum* mAspAT enhances the expression of its endogenous PEP-Case. However, there is no account on effect of AspAT overexpression on plant growth and productivity.

Reference may be made to yet another article by Zhou, Y., Cai, H., Xiao, J., Li, X., Zhang, Q. and Lian, X., entitled "Over-expression of aspartate aminotransferase genes in rice resulted in altered nitrogen metabolism and increased amino acid content in seeds" (2009, Theoretical and Applied Genetics, 118:1381-1390), wherein three AspAT genes from rice (OsAAT1-3) encoding chloroplastic, cytoplasmic, and mitochondrial AspAT isoenzymes, respectively and one AspAT gene from *E. coli* (EcAAT) were overexpressed in rice plant under the control of CaMV 35S promoter. The OsAAT1, OsAAT2, and EcAAT transformants showed significantly increased leaf AspAT activity and greater seed amino acid and protein contents. However no significant changes were found in leaf AspAT activity, seed amino acid content or protein content in OsAAT3 over-expressed plants.

Reference may be made to yet another article by Murooka, Y., Mori, Y. and Hayashi, M., entitled "Variation of the amino acid content of *Arabidopsis* seeds by expressing soyabean aspartate aminotransferase gene" (2009, Journal of Bioscience and Bioengineering, 94: 225-230), wherein AspAT5 encoding the chloroplast AspAT from Soyabean was linked to CaMV 35S promoter for achieving its over-expression in the *Arabidopsis* plant. Expression of AspAT5 in transformants caused 3-, 4-, 23-, and 50-fold increases in the contents of free glycine, alanine, asparagine, and Glu, respectively, in the $T_3$ seeds. However, a decrease in the contents of valine, tyrosine, isoleucine, leucine, and phenylalanine by several folds was also observed. Further, there is no report on effect of overexpression of AspAt on plant growth and productivity.

Reference may be made to yet another article by Yanagisawa, S., Akiyama, A., Kawaka, H., Uchimiya, H. and Miwa, T. entitled "Metabolic engineering with Dof1 transcription factor in plants: Improved nitrogen assimilation and growth under low-nitrogen conditions" (2004, Proceedings of the National Academy of Sciences (USA), 101:7833-7838), wherein over-expression of Dof1 transcription factor from maize improves N assimilation in transgenic *Arabidopsis* plants. Dof1 expressing plants showed up-regulation of genes encoding enzymes for C skeleton production, a marked increase of amino acid contents, and a reduction of the glucose level. The results suggest cooperative modification of C and N metabolisms on the basis of their intimate link. Elementary analysis revealed that the N content increased in the Dof1 transgenic plants (≈30%), indicating promotion of net N assimilation. However, effect of C N alteration on plant biomass or yield was not discussed.

Reference may be made to still another article by Takahashi, H., Takahara, K., Hashida, S., Hirabayashi, T., Fujimori, T., Kawai-Yamada, M., Yamaya, T., Yanagisawa, S, and Hirofumi Uchimiya, H., entitled "Pleiotropic Modulation of carbon and nitrogen metabolism in *Arabidopsis* plants overexpressing the NAD kinase2 gene" by (2009, Plant Physiology. 151:100-113), wherein transgenic *Arabidopsis* plants with over expression of NAD kinase2 (NADK2) along with NADK2 mutants were raised to investigate the impacts of altering NADP level on plant metabolism. Metabolite profiling revealed that NADP(H) concentrations were proportional to NADK activity in NADK2 overexpressors and in the NADK2 mutant. Several metabolites associated with the calvin cycle were also higher in the overexpressors, accompanied by an increase in overall Rubisco activity. Furthermore, enhanced NADP(H) production due to NADK2 overexpression increased N assimilation. Gln and Glu concentrations, as well as some other amino acids, were higher in the overexpressors. However, there is no clear evidence on role of NADK2 influencing C and N metabolism.

The improvement in the C and N status of plants is a major concern to improve productivity. However, there is no report yet which show enhancement of C and N levels and subsequent improvement in the biomass and yield of plant.

Further, no attempt has been made to co-over express three genes, viz. AspAT, GS and PEPCase, leading to enhanced status of C and N, biomass, and yield.

OBJECTIVES OF THE INVENTION

The main objective of the present invention is to provide an expression construct for enhancing the carbon, nitrogen, biomass and yield of plants which obviates the drawbacks of the hitherto known prior art as detailed above.

Another objective of the present invention is to provide an expression construct for co-overexpression of AspAT (SEQ ID NO: 1), GS (SEQ ID NO: 2). and PEPcase (SEQ ID NO: 3) wherein PEPCase efficiently captures $CO_2$ whereas the other two genes encoding for enzymes (AspAT and GS) have role in N assimilation, using the carbon backbone provided by PEPCase mediated reaction resulting in the enhancement of C and N status with improved biomass and yield of plants.

Yet another objective of the present invention is to raise transgenic plant exhibiting co-overexpression of genes AspAT, GS and PEPCase.

Still another objective of the present invention is to evaluate the expression of AspAT, GS and PEPCase genes in transgenic plants.

Still another objective of the present invention is to evaluate the transgenic plants for status of C and N, biomass and yield compared to wild plants.

SUMMARY OF THE INVENTION

Accordingly, the present invention provides an expression construct represented by SEQ ID NO. 7 for co-expression of the genes AspAT, GS and PEPCase comprising nucleotide sequences represented by SEQ ID NO: 1, SEQ ID NO: 2 and SEQ ID NO: 3, wherein SEQ ID NO: 1 represents AspAT genes, SEQ ID NO: 2 represents GS genes and SEQ ID NO: 3 represents PEPCase genes linked to at least one control sequence and a transcription terminator sequence, useful for enhancing the carbon, nitrogen, biomass and yield of plants as compared to wild type or untransformed plant.

In an embodiment of the present invention, the control sequence is preferably represented by SEQ ID NO: 4.

In another embodiment of the present invention, the transcription terminator sequence is represented by SEQ ID NO: 5.

In an embodiment, the present invention provides an expression construct prepared from the cytosolic AspAT-gene from soyabean, cytosolic GS gene from tobacoo and cytosolic PEPCase gene from maize.

In another embodiment of the present invention, the polynucleotide having SEQ ID No: 7 is overexpressed in plants.

In still another embodiment of the present invention, the control sequence used is a constitutive promoter selected from the group consisting of CaMV 35S promoter, rubisco promoter, ubiquitin promoter, actin promoter.

In still another embodiment of the present invention, the terminator used is preferably selected from the group consisting of Nos terminator and CaMV 3' UTR.

In still another embodiment of the present invention, a process for preparing the expression construct wherein the process comprising the steps of:
  i) amplifying cDNA sequences encoding genes represented by SEQ ID NO: 1 using primers represented by SEQ ID NO: 10 and SEQ ID NO: 11, SEQ ID NO: 2 using primers represented by SEQ ID NO: 8 and SEQ ID NO: 9 and SEQ ID NO: 3 using primers represented by SEQ ID NO: 12 and SEQ ID NO: 13;
  ii) cloning independently the amplified product of SEQ ID NO: 1, 2 and 3 as obtained in step (i) into pGEM®-T Easy Vector (cloning vector, Promega, USA);
  iii) digesting independently the plasmid from the positive clones as obtained in step (ii) along with pCAMBIA 1302 and further ligating the digested gene products and pCAMBIA 1302 and transforming into E. coli DH5 α cells;
  iv) sequencing the plasmid from the positive colonies obtained in step (iii) confirming the inframe cloning of AspAT::pCAMBIA1302; GS::pCAMBIA1302 and PEPCase::pCAMBIA 1302.
  v) amplifying the products obtained in step (iv) by using primers represented by SEQ ID NO: 10 and SEQ ID NO: 16; SEQ ID NO: 14 and SEQ ID NO: 15 and SEQ ID NO: 17 and SEQ ID NO: 18.
  vi) cloning, digesting, ligating and sequencing was again performed independently for the amplified GS coding sequence to form GS+pCAMBIA1302 which was further digested and ligated with the plasmids of positive clones of amplified AspAT coding sequence to form AspAT+GS+pCAMBIA1302 expression cassette;
  vii) ligating the digested plasmids of positive clones of amplified PEPCase coding sequence with the destination pCAMBIA1302 which was previously cloned with the AspAT+GS+ expression cassette as obtained in step (vi) such that the genes AspA, GS and PEPCase were controlled by independent CaMV 35S promoter and Nos transcriptional terminator to form single plant expression construct AspAT+GS+PEPCase represented by SEQ ID NO: 7.

In still another embodiment of the present invention, a process for enhancing the carbon, nitrogen, biomass and yield of plants using the expression construct, wherein the said process comprising the steps of:
  a) transforming Agrobacterium tumefacians strain with the expression construct as claimed in claim 1;
  b) transforming the explants with the recombinant Agrobacterium tumefacians strain as obtained in step (a);
  c) selecting the transformed explants of step (b) to obtain the desired transformed plants having enhanced level of carbon, nitrogen, biomass and yield of plants as compared to wild type plant.

In still another embodiment of the present invention, a process wherein the transformed plants display an increase of about 45-50% in PEPCase activity, at least 55% in GS activity and 55-60% in AspAT activity as compared to wild type, resulting in increase in carbon and nitrogen levels in the plant.

In another embodiment of the present invention, the Agrobacterium strain provided is selected from a group consisting of GV3101 with ATCC number Agrobacterium tumefaciens (GV3101 (pMP90RK) (C58 derivative) ATCC® Number: 33970 Reference: Hayashi H, Czaja I, Lubenow H, Schell J, Walden R. 1992.

In yet another embodiment of the present invention, the transformed plants are selected from the group consisting of grain crops, pulses, vegetable crops, oilseed crop and ornamentals.

In yet another embodiment, the transformed plants are selected from the group consisting of arabidopsis, tomato, potato, tobacco, maize, wheat, rice, cotton, mustard, pigeon pea, cowpea, pea, sugarcane, soya bean and sorghum.

In still another embodiment, the transformed plants as compared to wild type display increased yield and/or biomass, indicated by increased seed yield and/or pod yield.

In still another embodiment, the transformed plants display enhanced growth characteristics characterized by increased shoot fresh weight, shoot dry weight, root fresh and dry weight as compared to wild type or untransformed plant.

In yet another embodiment of the present invention, the transformed plant shows enhanced levels of carbon, nitrogen, biomass and yield as compared to wild plants.

In still another embodiment of the present invention, the expression and functionality of over expressed enzymes in transgenic plants is evaluated.

In yet another embodiment of the present invention, the selectable marker used is hpt gene (hygromycin phosphotransferase) represented by SEQ ID NO: 6 for hygromycin resistance controlled by duplicated CaMV 35S promoter and terminated by CaMV 3'UTR (polyA signal).

In another embodiment of the present invention, biochemical assays and RT-PCR were performed to evaluate the expression of introduced genes and the functionality of over expressed enzymes in transgenic plants.

In a further embodiment of the present invention, the transgenic plants were investigated for different growth and yield parameters and compared to wild plants cultivated under the same conditions.

BRIEF DESCRIPTION OF THE ACCOMPANYING DRAWINGS

DETAILED DESCRIPTION OF THE INVENTION

Figure 1:
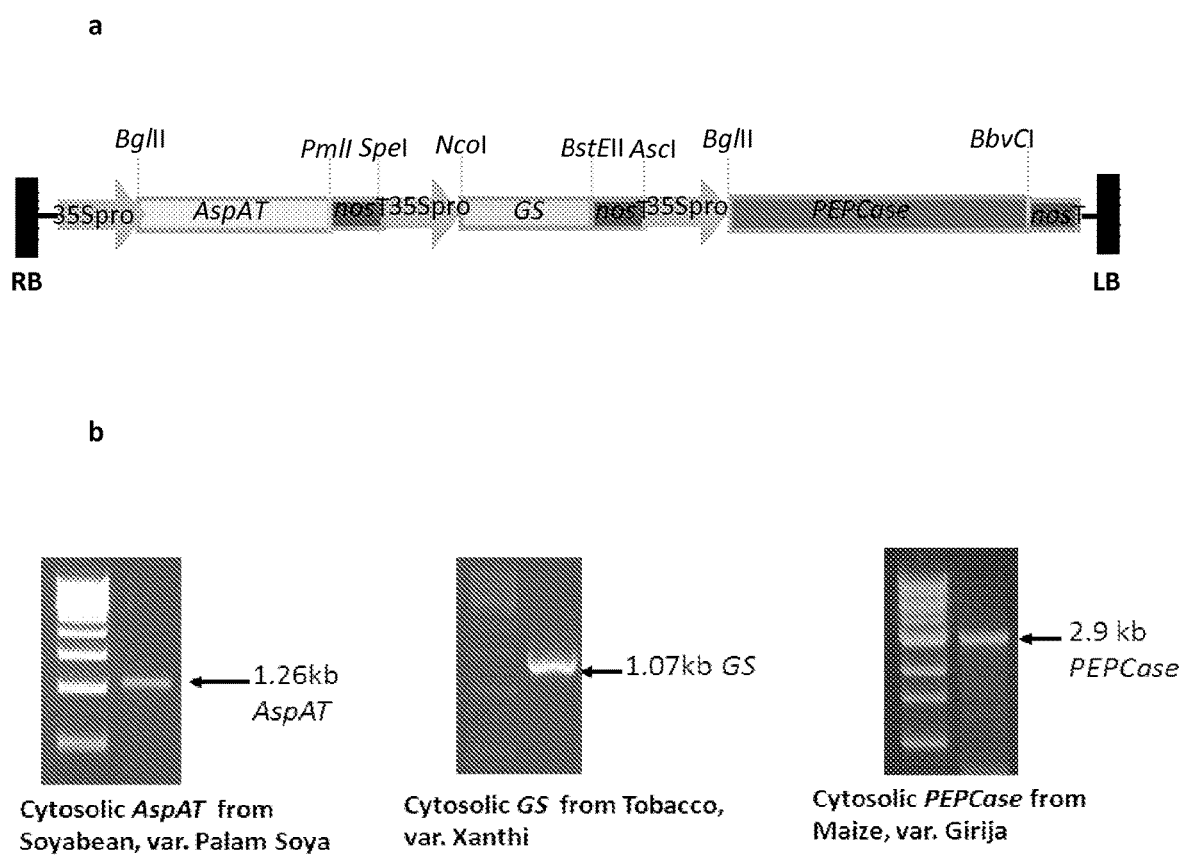
FIG. 1 represents a schematic view of T-DNA region of plant transformation vector pCAMBIA1302 for co-overexpression of AspAT, GS and PEPCase (a) and amplification of coding sequences for AspAT, GS and PEPCase from respective plant sources (b) as discussed in Examples 1 to 4.

The present invention relates to genetic engineering of C and N metabolism in plants. In particular, the present invention relates to an expression construct for co-overexpression of AspAT, GS and PEPCase for concomitant alteration in the enzymes involved in C and N assimilation or utilization and/or their expression in order to engineer plants with increased C and N levels thereby promoting better growth and biomass production and enhanced yield.

The term "vector" refers to a construct made up of nucleic acids wherein gene from a foreign source can be ligated and isolated when needed. The construct is usually a plasmid (i.e. extra chromosomal self replicating nucleic acid) and is propagated, for example bacterial cell of E. coli. The vector in the present invention was used to transfer the gene from one source to another.

The term "gene" refers to the sequence of nucleic acids that can produce a polypeptide chain.

The term "gene expression" refers to the level/amount of RNA (i.e. sequence of ribonucleic acid) of choice transcribed (i.e. the process of synthesis of RNA by DNA) by DNA (i.e. sequence of deoxyribonucleic acid). When the gene was transcribed in higher amounts as compared to the control, it was referred to as "over-expression" of gene.

The term "selectable marker" refers to a gene, which allows a cell to survive in the presence of an otherwise toxic antibiotic The term "transgenic plant" refers to genetically transformed plants with stable integration of introduced gene in to its genome The term "promoter" refers to the specific DNA sequence, usually located upstream (5') to the DNA sequence involved in transcription, wherein the enzyme RNA polymerase binds for the process of transcription. "Constitutive promoters" direct expression of the gene in all tissues and during all periods regardless of the surrounding environment and development stage of the organism.

The term 'expression cassettes" refers to vector comprising of (a) a constitutive promoter; (b) all the three genes cloned 3' to the constitutive promoter, (c) a polyadenylation signal located 3' to the coding sequence.

and capable of passing genetic information on to successive generations.

'Wild-type" plants are untransformed plants.

The term "$T_0$" refers to the first set of genetically transformed plants that can be identified and selected upon growth in presence of a selection agent antibiotic, for which the transgenic plant contains the corresponding resistance gene. The term "$T_1$" refers to the generation of plants obtained after self-fertilization of the flowers of $T_0$ generation plants, previously selected as being transgenic. "$T_2$" plants are generated from $T_1$ plants, and so on. The present invention will be illustrated in greater details by the following examples.

EXAMPLES

The following examples are given by way of illustration of the present invention and therefore should not be construed to limit the scope of the present invention.

Sequences of the primers used in the present invention are listed as follows:

| Name of the sequence | Sequence | | | | | | Purpose | Sequence ID No. |
|---|---|---|---|---|---|---|---|---|
| AspAT cDNA sequence | atggcttctc cacctcgttc ccaagtccag cttgttttga aaggaatata tttggggctg ggaactggtt atatacttgc tctgtcaaaa ctggaagacc aaccccactg tcaaaagctt gatgcagatg | acgacagcat gtgctcccga ttaagctcaa atgtagtgag ttccgatcgt acagccctgc ctttaagagt caacaccaac cataccgcta ttggttctgc gtgtggatcc tgttaccttt cccaacctgt | ctccgcttct agatcctatc cttgggagtt gcgagttgaa tgggcttgct tattcaagac tgggggtgaa ttggggcaat ctatgctcca tccatctgga aaccctgag ctttgacagt tcgtttgttt | ccaacctccg ctcggggtaa ggtgcttacc cagcaactca gatttaata aacagggtta ttttttggcta caccgaagg gcaacacgag tctattgttt caatgggagc gcttatcagg gttgctgatg | cttctgattc ctgtcgctta gaactgagga taaatgacgt aattgagtgc ccactgttca aacactatca tttcaactt gacttgactt tgctacatgc agattaggca gttttgctag gaggcgaatt | cgtcttcaat 60 taacaaagat 120 aggaaaacct 180 gtcacgcaca 240 taagcttatt 300 atgcttgtct 360 ccaacggact 420 agcaggcttg 480 tcaaggactt 540 atgcgcacat 600 gctaataaga 660 tggaagtcta 720 gctggtagca 780 | Represents nucleotide sequences of AspAT genes for making an expression | 1 |

-continued

| Name of the sequence | Sequence | | | | | | Purpose | Sequence ID No. |
|---|---|---|---|---|---|---|---|---|
| | caaagctatg | caaagaatct | gggtctttat | ggggaacgtg | ttggcgcctt | aagcattgtc 840 | | |
| | tgcaagtcag | ctgatgttgc | aagcagggtt | gagagccagc | tgaagctagt | gattaggccc 900 | | |
| | atgtactcaa | gtcctcccat | tcatggtgca | tccattgtgg | ctgccattct | caaggaccgg 960 | | |
| | aatttgttca | atgactggac | tattgagttg | aaggcaagtc | ctgatcgcat | catcagtatg 1020 | | |
| | cgccaagaac | ttttcgatgc | tttatgttcc | agaggcacac | ctggcgattg | gagtcacatt 1080 | | |
| | atcaaacaga | ttggaatgtt | tactttcact | ggattgaatg | cggaacaagt | ttccttcatg 1140 | | |
| | actaaagagt | tccatatata | catgacatct | gatgggagga | ttagcatggc | tggtctgagt 1200 | | |
| | tccaaaactg | tcccacttct | ggcggatgcg | atacatgcag | ctgtaacccg | agttgtctaa 1260 | | |
| GS cDNA sequence | atggctcatc | tttcagatct | cgttaatctc | aatctctctg | actccactca | gaaaattatt 60 | Represents nucleotide sequences of GS genes for making an expression construct | 2 |
| | gctgaataca | tatggattgc | tggatcagga | atggacgtca | ggagcaaagc | cagaacactt 120 | | |
| | tctggacctg | ttgatgatcc | ttcaaagctt | cccaaatgga | attatgatgg | ttctagcaca 180 | | |
| | ggacaagctc | ctggagaaga | cagtgaacat | ctcaagcaat | tttcaaggat 240 | | | |
| | ccattcagaa | ggggcaacaa | tatcttggtc | atttgtgatt | gttacacccc | agctggtgaa 300 | | |
| | cccattccaa | caaacaaaag | gcacagtgct | gccaagattt | tcagccaccc | tgatgttgtt 360 | | |
| | gttgaggaac | cctggtatgg | tcttgagcaa | gaatacacct | tgttgcaaaa | agatatcaat 420 | | |
| | tggcctcttg | gatggcctct | tggtggtttt | cctggaccac | agggaccata | ctattgcgga 480 | | |
| | attggagctg | gaaaggtctt | tggacgcgat | atcgttgact | ctcattataa | ggcatgtctc 540 | | |
| | tatgctggga | ttaacatcag | tggtatcaat | ggagaagtga | tgcccggaca | gtgggaattt 600 | | |
| | caagttgac | cttcagttgg | catttcagca | gctgatgaat | tgtgggcagc | tcgttacatt 660 | | |
| | cttgagagga | ttactgagat | tgctggagtt | gtggtctcat | ttgaccccaa | acctattccg 720 | | |
| | ggtgactgga | atggtgctga | agctcacaca | aactacagca | caaagtctat | gaggaatgaa 780 | | |
| | ggaggctatg | aagtcattaa | gaaggcaatt | gagaaccttg | gactgaggca | caggagcat 840 | | |
| | attgcagcat | atggtgaagg | caacgagcgt | cgtctcactg | aagacacga | aacagctgac 900 | | |
| | atcaacacat | tcaaatgggg | agttgcgaac | cgtggtgcat | ctattgcgtg | gggaagagac 960 | | |
| | acggagagag | aagggaaggg | atacttcgag | gataggaggc | ctgcttcgaa | tatggatcca 1020 | | |
| | ttcgtcgtga | cttccatgat | tgctgagacc | actatcctat | ccgagcttg | a 1071 | | |
| PEPCase cDNA sequence | ctcgtcgacc | gcttcctcaa | catcctccag | gacctccacg | ggcccagcct | tcgcgaattt 180 | Represents nucleotide sequences of PEPCase genes for making an expression construct | 3 |
| | gtccaggagt | gctacgaggt | ctcagccgac | tacgagggca | aggagacac | gacgaagctg 240 | | |
| | ggcgagctcg | gcgccaagct | cacggggctg | gccccgccg | acgccatcct | cgtggcgagc 300 | | |
| | tccatcctgc | acatgctcaa | cctcgccaac | ctggccgagg | aggtgcagat | cgcgcaccgc 360 | | |
| | cgccgcaaca | gcaagctcaa | gaaaggtggg | ttcgccacg | agggctccgc | caccaccgag 420 | | |
| | tccgacatcg | aggagacgct | caagcgcctc | gtgtccgagg | tcggcaagtc | cccgagagg 480 | | |
| | gtgttcgagg | cgctcaagaa | ccagaccgtc | gacctcgtct | tcaccgcgca | tcctacgcag 540 | | |
| | tccgcccgcc | gctcgctcct | gcaaaaaaat | gccaggatcc | gaaattgtct | gacccagctg 600 | | |
| | aatgccaagg | acatcactga | cgacgacaag | caggagctcg | atgaggctct | gcagagagag 660 | | |
| | atccaagcag | ccttcaagaac | cgatgaaatc | caggagggcac | aacccaccccc | gcaggccgaa 720 | | |
| | atgcgctatg | ggatgagctca | catccatgag | actgtatgga | agggtgtgcc | taagttcttg 780 | | |
| | cgccgtgtgg | atacagcct | gaagaatatc | ggcatcaatg | agccgcttcc | ctacaatgtt 840 | | |
| | tctctcattc | ggttctcttc | ttgatgggt | ggtgaccgcg | atggaaatcc | aagagttacc 900 | | |
| | ccggaggtga | caagagatgt | atgcttgctg | gccagaatga | tggctgcaaa | cttgtacatc 960 | | |
| | gatcagattg | aagagctgat | gtttgagctc | tctatgtggc | gctgcaacga | tgagcttcgt 1020 | | |
| | gttcgtgccg | aagagctcca | cagttcgtct | ggttccaaag | ttaccaagta | ttacatagaa 1080 | | |
| | ttctggaagc | aaattcctcc | aaacgagccc | taccgggtga | ctaggcca | tgtaagggac 1140 | | |
| | aagctgtaca | acacacgcga | gcgtgctcgc | catctgctgg | cttctggagt | ttctgaaatt 1200 | | |
| | tcagcggaat | cgtcatttac | cagtatcgaa | gagttccttc | agccacttga | gctgtgctac 1260 | | |
| | aaatcactgt | gtgactgcgg | cgacaaggcc | atcgcggacg | ggagcctctt | ggacctcctg 1320 | | |
| | cgccaggtgt | tcacgttcgg | gctctccctg | gtgaagctgg | acatccggca | ggagtcggca 1380 | | |
| | cggcacaccg | acgtgatcga | cgccatcacc | acgcacctcg | gcatcgggtc | gtaccgcgag 1440 | | |
| | tggcccgagg | acaagaggca | ggagtggctg | ctgtcggagc | tgcgaggcaa | gcgcccgctg 1500 | | |
| | ctgccccgg | accttccccca | gaccgacgag | atcgccagtg | tcatcggcgc | gttccacgtc 1560 | | |
| | ctcgcggagc | tcccgcccga | cagcttcggc | cctacatca | tctccatggc | gacggccccc 1620 | | |
| | tcggacgtgc | tcgccgtgga | gctcctgcag | cgcgagtgcg | gcgtgcgcca | gccgctgccc 1680 | | |
| | gtggtgccgc | tgttcgagag | gctggccgac | ctgcagtcgg | cgcccgcgtc | cgtggagcgc 1740 | | |
| | ctcttctcgg | tggactggta | catggaccgg | atcaagggca | agcagcaggt | catggtcggc 1800 | | |
| | tactccgact | ccggcaagga | cgccggccgc | cctgtccgcgg | cgtgccgact | gtacagggcg 1860 | | |
| | caggaggaga | tggcgcaggt | ggccaagcgc | tacggcgtca | agctcaccttg | gttccacggc 1920 | | |
| | cgcggaggca | ccgtgggcag | gggtggcggg | cccacgcacc | ttgccatcct | gtcccagccg 1980 | | |
| | ccggacacca | tcaacgggtc | catccgtgtg | acggtgcagg | gcgaggtcat | cgattctgc 2040 | | |
| | ttcggggagg | agcacctgtg | cttccagact | ctgcagcgct | tcacggccgc | cacgctggag 2100 | | |
| | cacgcgcatgc | acccgccggt | ctctcccaag | cccgagtggc | gcaagctgcc | ggacagagatg 2160 | | |
| | gcggtctgtgg | ccacggaggta | gtaccgctcc | tcgtcgtca | aggagcgcg | cttcgtccggc 2220 | | |
| | tacttcagat | cggctacacc | ggagaccgag | tacgggagga | tgaacatcgg | cagccggcca 2280 | | |
| | gccaagagga | ggccccggcg | cggcatcacg | accctgcgcg | ccatccctg | gatcttctcg 2340 | | |
| | tggaccagcaga | ccaggttcca | cctcccgtg | tggctggag | tcggcgccgc | attcaagttc 2400 | | |
| | gccatcgaca | aggacgtcag | gaacttccag | gtctcaaag | agatgtacaa | cgagtggccca 2460 | | |
| | ttcttcaggg | tcacctgga | cctgctgga | atggtttttc | ccaagggaca | cccggcatt 2520 | | |
| | gccggcttgt | atgacgagct | gcttgtggcg | gaagaactca | agcccttgg | gaagcagctc 2580 | | |
| | agggacaaat | acgtggagac | acagcagctt | ctcctccaga | tcgctgggca | caggatatt 2640 | | |
| | cttgaaggcg | atccattcct | gaagcagggg | ctggtgctgc | gcaaccccta | catcaccacc 2700 | | |
| | ctgaacgtgt | tccaggccta | cacgctgaag | cggataaggg | acccaacttt | caaggtgacg 2760 | | |
| | ccccagccgc | cgctgtccaa | ggagttcgcc | gacgagaaca | agcccgccgc | actggttcaag 2820 | | |

| Name of the sequence | Sequence | Purpose | Sequence ID No. |
|---|---|---|---|
| | ctgaacccgg cgagcgagta cccgcccggc ctggaagaca cgctcatcct caccatgaag 2880<br>ggcatcgccg ccggcatgca gaacactggc tag 2913 | | |
| CaMV 35S promoter sequence | catggagtca aagattcaaa tagaggacct aacagaactc gccgtaaaga ctggcgaaca 60<br>gttcatacag agtctcttac gactcaatga caagaagaaa atcttcgtca acatggtgga 120<br>gcacgacaca cttgtctact ccaaaaatat caaagataca gtctcagaag accaaagggc 180<br>aattgagact tttcaacaaa gggtaatatc cggaaacctc ctcggattcc attgcccagc 240<br>tatctgtcac tttattgtga agatagtgga aaaggaaggt ggctcctaca aatgccatca 300<br>ttgcgataaa ggaaaggcca tcgttgaaga tgcctctgcc gacagtggtc ccaaagatgg 360<br>accccacc acgaggagca tcgtggaaaa agaagacgtt ccaaccacgt cttcaaagca 420<br>agtggattga tgtgatatct ccactgacgt aagggatgac gcacaatccc actatccttc 480<br>gcaagaccct tcctctatat aaggaagttc atttcatttg gagagaacac gggggact 538 | Represents control sequence | 4 |
| nos (nopaline synthase) 3'UTR (poly-Asignal) sequence | cgttcaaaca tttggcaata aagtttctta agattgaatc ctgttgccgg tcttgcgatg 60<br>attatcatat aatttctgtt gaattacgtt aagcatgtaa taattaacat gtaatgcatg 120<br>acgttattta tgagatgggt ttttatgatt agagtcccgc aattatacat ttaatacgcg 180<br>atagaaaaca aaatatagcg cgcaaactag gataaattat cgcgcgcggt gtcatctatg 240 | Represents transcription terminator sequence | 5 |
| hygromycin-phosphotransferase | ctatttcttt gccctcggac gagtgctggg gcgtcggttt ccactatcgg cgagtacttc 60<br>tacacagcca tcggtccaga cggccgcgct tctgcgggcg atttgtgtac gcccgacagt 120<br>cccggctccg atcggacga ttgcgtcgca tcgaccctgc gcccaagctg catcatcgaa 180<br>attgccgtca accaagctct gatagagttg gtcaagacca atgcggagca tatacgcccg 240<br>gagtcgtggc gatcctgcaa gctccggatg cctccgcctc aagtagcgcg tctgctgctc 300<br>catacaagcc aaccacggcc tccagaagaa gatgttggcg acctgtatt gggaatcccc 360<br>gaacatcgcc tcgctccagt caatgaccgc tgttatgcgg ccattgtccg tcaggacatt 420<br>gttggagccg aaatccgcgt gcacgaggtg ccggacttcg ggcagtcct cggcccaaag 480<br>catcagctca tcgagagcct gcgcgacgga cgcactgacg tgtcgtcca tcacagtttg 540<br>ccagtgatac acatgggat cagcaatcgc gcatatgaaa tcacgccatg tagtgtattg 600<br>accgattcct tgcggtccga atgggccgaa cccgcctc tggctaagat cggccgcagc 660<br>gatcgcatcc atagcctccg cgaccggttg tagaacagcg ggcagttcgg tttcaggcag 720<br>gtcttgcaac gtgacaccct gtgcacggcg ggagatgcca taggtcaggc tctcgctaaa 780<br>ctccccaatg tcaagcactt ccggaatcgg agcgcggcc gatgcaaagt gccgataaac 840<br>ataacgatct tgtagaaac catcggcgca gctatttacc gcaggacat atccacgccc 900<br>tcctacacg aagctgaaag cacgagattc ttcgccctcc gagagctgca tcaggtcgga 960<br>gacgctgtcg aacttttcga tcagaaactt ctcgacagac gtcgcggtga gttcaggctt 1020<br>tttcat 1026 | Represents hpt gene (hygromycin phosphotransferase) for hygromycin resistance | 6 |
| expression cassettes for AspAT, GS and PEPCase coding sequences, cloned under control of CamV 35S promoter (__) and Nos terminator (__) in pCAMBIA 1302 | <u>catggagtcaaagattcaaatagaggacctaacagaactcgccgtaaagactggcgaacagttcataca</u><br><u>gagtctcttacgactcaatgacaagaagaaaatcttcgtcaacatggtggagcacgacacacttgtctact</u><br><u>ccaaaaatatcaaagatacagtctcagaagaccaaagggcaattgagacttttcaacaaagggtaatatc</u><br><u>cggaaacctcctcggattccattgcccagctatctgtcactttattgtgaagatagtggaaaaggaaggtgg</u><br><u>ctcctacaaatgccatcattgcgataaaggaaaggccatcgttgaagatgcctctgccgacagtggtccca</u><br><u>aagatggaccccacccacgaggagcatcgtggaaaaagaagacgttccaaccacgtcttcaaagcaag</u><br><u>tggattgatgtgatatctccactgacgtaagggatgacgcacaatcccactatccttcgcaagaccct</u><br><u>tcctctatataaggaagttcatttcatttggagagaacacgggggact</u>cttgaccatggt|agatct|tatg<br>gcttctcacgacagcatctccgcttctccaacctccgcttctgattccgtcttcaatcacctcgttcgtg<br>ctcccgaagatcctatcctcggggtaactgtcgcttataacaaagatccaagtccagttaagctcaacttggg<br>agttggtgcttaccgaactgaggaaggaaaacctcttgtttttgaatgtagtgaggcgagttgaacagcaact<br>cataaatgacgtgtcacgcaacaaggaatatattccgatcgttgggcttgctgattttaataaattgagtgct<br>aagcttatttttggggctgacagccctgctattcaagacaacaggggtaccactgttcaatgcttgtctgaac<br>tggttctttaagagttggggtgaattttggctaaacactatcaccaacggactatatacttgccaacaccaa<br>cttgggcaatcacccgaaggttttcaacttagcaggcttgtctgtcaaaacataccgctactatgctccagc<br>aacacgaggactttgacttcaaggacttcgttgcttctgctccatctattgtttgctaca<br>tgcatgcgcacataaccccactggtgtggatccaacccttgagcaatggggacagattaggcagctaataag<br>atcaaaagctttgttaccttctttgacagtgcttatcagggttttgctagtggaagtctagatgcagatgccca<br>acctgttcgtttgtttgttgctgatggaggcgaattgctggtagcacaaagctatgcaaagaatctgggtctttt<br>atggggaacgtgttggcgccttaagcattgtctgcaagtcagctgatgttgcaagcagggttgagagccagc<br>tgaagctagtgattaggccccatgtactcaagtcctcccattcatggtgcatccattgtggctgccattctcaag<br>gaccggaatttgttcaatgactgcatattgagttgaaggcaatggctgatcgcatcatcagtatcgccaag<br>aactttcgatgcttatgttccagaggcacacctggcgattggagtcacattatcaaacagattggaatgttt<br>actttcactggattgaatgcggaacaagttttccttcatgactaaagagttccatatatacatgacatctgatgg<br>gaggattagcaggctggtctgagttccaaaactgtcccacttctggcggatgcgatacatgcagctgtaacc<br>cgagttgtctaa|acg|<br>|tgt|gaattggtgaccagctcgaatttcccccgat<u>cgttcaaacatttggcaataaagtttcttaagattgaatc</u><br><u>ctgttgccggtcttgcgatgattatcatataatttctgttgaattacgttaagcatgtaataattaacatgtaa</u> | Represents an expression construct for co-expression of the genes AspAT, GS and PEPCase SpeI<br><br><br><br><br><br><br><br><br><br>PrnII | 7 |

| Name of the sequence | Sequence | Purpose | Sequence ID No. |
|---|---|---|---|
| | tgcatgacgttatttatgagatgggttttttatgattagagtcccgcaattatacatttaatacgcgatagaaa acaaaatatagcgcgcaaactaggataaattatcgcgcgcggtgtcatctatgt SpecI tactagatcgggaattaa<span style="border:1px solid">actagt</span>aatggcgaatgctagagcagcttgagcttggatcagattgtcgtttccc gccttcagtttagcttcatggagtcaaagattcaaatagaggacctaacagaactcgccgtaaagactggc gaacagttcatacagagtctcttacgactcaatgacaagaagaaaatcttcgtcaacatggtggagcacg acacacttg tctactccaaaaatatcaaagatacagtctcagaagaccaaagggcaattgagacttttcaacaaagggt aatatccggaaacctcctcggattccattgcccagctatctgtcactttattgtgaagatagtggaaagga aggtggctcctacaaatgccatcattgcgataaaggaaaggccatcgttgaagatgcctctgccgacagtg gtcccaaagatggaccccccacccacgaggagcatcgtggaaaaagaagacgttccaaccacgtcttcaaa gcaagtggattgatgtgatatctccactgacgtaagggatgacgcacaatcccactatccttcgcaagacc c ttcctctatataaggaagttcatttcatttggagagaacacgggggactctt<span style="border:1px solid">gaccat</span>ggctcatctttca GS coding sequence → gatctcgttaatctcaatctctctgactccactcagaaaattattgctgaatacatatggattggtggatcagg aatggacgtcaggagcaaagccaaacactttctggacctgttgatgatccttcaaagcttcccaaatggaa ttatgatggttctagcacaggacaagctcctggagaagacagtgaaggagatcctatatcctcaagcaattttc aaggatccattcagaaggggcaacaatatcttggtcatttgtgattgttacaccccagctggtgaacccattc caacaaacaaaggcacagtgctgccaagattttcagccaccctgatgttgttgttgaggaaccctggtatg gtcttgagcaagaatacaccttgttgcaaaaagatatcaattggcctcttggatggctcttggtggttttcct ggaccacaggacctactattgcggagttggagctggaaaggtctttggacgcgatatcgttgactctcatt ataaggcatgtctctatgctgggattaacatcagtggtatcaatggagaagtgatgccccgacagtgggaat ttcaagttggaccttcagttggcatttcagcagctgatgaattgtgggcagctcgttacattcttgagaggatt actgagattgctggagttgtggtctcatttgaccccaaacctattccgggtgactggaatggtgctggagctc acacaaactacagcacaagctctatgaggaatgaaggagcctgaagtcattaagaaggtcaattgagaa ccttggactgaggcacaaggagcatattgcagcatatggtgaaggcaacgagcgtcgtctcactggaagac acgaaacagctgacatcaacacattcaaatggggagttgcgaaccgtggtgcatctattcgtgtgggaaga gacacggagagagaagggaagggatacttcgaggataggaggcctgcttcgaatatggatccattcgtcgt gacttccatgattgctgagaccactatcctatccgagcctga<span style="border:1px solid">ggtcacc</span>ag ctcgaatttccccgatcgttcaaacatttggcaataaagtttcttaagattgaatcctgttgccggtcttgcga tgattatcatataatttctgttgaattacgttaagcatgtaataattaacatgtaatgcatgacgttatttatg agatgggttttatgattagagtcccgcaattatacatttaatacgcgatagaaaacaaaatata gcgcgcaaactaggataattatcgcgcgcggtgtcatctatgttactagatcgggaattaaactatcagt AscI gtttgacaggatatattggcg<span style="border:1px solid">ggcgcgcc</span>aatggcgaatgctagagcagcttgagcttggatcagattgtcg ttttcccgccttcagtttagcttcatggagtcaaagattcaaatagaggacctaacagaactcgccgtaaaga ctggcgaacagttcatacagagtctcttacgactcaatgacaagaagaaaatcttcgtcaacatggtggag cacgacacacttgtctactccaaaaatatcaaagatacagtctcagaagaccaaagggcaattgagactt ttcaacaagggtaatatccggaaacctcctcggattccattgcccagctatctgtcactttattgtgaagat agtggaaaaggaaggtggctcctacaaatgccatcattgcgataaaggaaaggccatcgttgaagatgcc tctgccgacagtggtcccaaagatggaccccccacccacgaggagcatcgtggaaaaagaagacgttccaa ccacgtcttcaaagcaagtggattgatgtgatatctccactgacgtaagggatgacgcacaatcccactat ccttcgcaagacccttcctctatataaggaagttcatttcatttggagagaacacgggggactcttgacca BglII PEPCase coding sequence → tggt<span style="border:1px solid">agatct</span>tatggcgtcgaccaaggctcccggccccggcgagaagcaccactccatcgacgcgcagctc cgtcagctggtcccaggcaaggtctccgaggacgacaagctcatcgagtacgatgcgctgctcgtcgaccgc ttcctcaacatcctccaggacctccacgggcccagccttcgcgaatttgtccaggagtgctacgaggtctcag ccgactacgagggcaaaggagacacgacgaagctgggcgagctcggcgccaagctcacggggctggccc cgccgacgccatcctcgtggcgagctccatcctgcacatgtgctcaacctcgccaacctggccgaggaggtgca gatcgcgcaccgcgccgcaacagcaagctcaagaaaggtgggttcgccgacgagggctccgacaccacc gagtccgacatcgaggagacgctcaagcgcctcgtgtccgaggtcggcaagtccccgaggaggtgttcga ggcgctcaagaaccagaccgtcgacctcgtcttcaccgcgcatcctacgcagtccgcccgccgctcgtcctg caaaaaaatgccaggatccgaattgtctgacccagctgaatgccaaggacatcactgacgacgacaagc aggagctcgatgaggctctgaagagagagatccaagcagccttcagaaccgatgaaatcaggagggcac aacccaccccgcaggccgaaatgcgctatgggatgagctcatccatgagactgtatggaagggtgtgcct aagttcttcgccgtgtggatacagccctgaagaatatcggcatcaatgagcgccttcctacaatgtttctct cattcggttctcttcttggatgggtggtgaccgcgatggaaatccaagagttaccccggaggtgacaagaga tgtatgcttgctggccagaatgatggctgcaaacttgtacatcgatcagattgaagagctgatgtgttgagctct ctatgtggcgctcaacgatgagcttcgtgttcgtgccgaagagctccacagttcgtctgttccaaagttacc aagtattacatagaattctggaagcaaattcctccaaacgagccctaccgggtgatactaggccatgtaagg gacaagctgtacaacacacgcgagcgtgctcgccatctgctggcttctggagtttctgaaatttcagcggaat cgtcatttaccagtatcgaagagttccttgagccacttgagctgtgctacaaatcactgtgtgactgcggcga caaggccatcgcggacgggagcctcctggacctcctgcgccaggtgttcacgttcgggctctccctggtgaa gctggacatccggagtggagctggagacaagaggcaggagtggctgctgtcggagctgcgaggcaagcgccc gctgctgccccggacctttcccagaccgacgagatcgcgacgtcatcggcgcgttccacgtcctcgcgga gctccgcccgacagcttcggcccctacatcatctccatggcgacggccctcggacgtgctcgccgtggag ctcctgcagcgcgagtgcggcgtgcgccagccgctgccccgtggtgccgctgttcgagaggctggccgacctg cagtcggcgcccgcgtccgtggagcgcctcttctcggtggactggtacatggaccggatcaagggcaagcag | | |
| | | NeaI BstEII | |

| Name of the sequence | Sequence | Purpose | Sequence ID No. |
|---|---|---|---|
| | caggtcatggtcggctactccgactccggcaaggacgccggccgcctgtcc gcggcgtggcagctgtacagggcgcaggaggagatggcgcaggtggccaagcgctacggcgtcaagctca ccttgttccacggccgcggaggcaccgtgggcaggggtggcgggcccacgcaccttgccatcctgtcccagc cgccggacaccatcaacgggtccatccgtgtgacggtgcagggcgaggtcatcgagtttctgcttcggggagg agcacctgtgcttccagactctgcagcgcttcacggccgccacgctggagcacggcatgcacccgccggtct ctcccaagcccgagtggcgcaagctcatggacgagatggcggtcgtgccacggaggagtaccgctccgtc gtcgtcaaggaggcgcgcttcgtcgagtacttcagatcggctacaccggagaccgagtacgggaggatgaa catcggcagccggccagccaagaggagcccggcggcggcatcacgaccctgcgcgccatccctggatct tctcgtggaccagaccaggttccacctccccgtggctgggagtcggcgccgcattcaagttcgccatcga caaggacgtcaggaacttccaggtcctcaaagagatgtacaacgagtggccattcttcagggtcaccctgga cctgctggagtggttttcgccaaggagacccggcattgccggcttgtatgacgagctgcttgtggcggaa gaactcaagcccttttgggaagcagctcagggacaaatacgtggagacacagcagcttctccttccagatcgct gggcacaaggatattcttgaaggcgatccattcctgaagcaggggctggtgctgcgcaacccctacatcacc accctgaacgtgttccaggcctacacgctgaagcggataagggaccccaacttcaaggtgacgccccagcc gccgctgtccaaggagttcgccgacgagaacaagcccgccggactggtcaagctgaacccgg cgagcgagtaccgcccggcctggaagacacgctcatcctcaccatgaagggcatcgccgccggcatgcag <br><br>                    BbmCI        PrnII <br> aacactggctag[gctgagga][cacgtg]tgaattggtgaccagctcgaatttccccgatcgttcaaacatttgg caataaagtttcttaagattgaatcctgttgccggtcttgcgatgattatcatataatttctgttgaattacgt taagcatgtaataattaacatgtaatgcatgacgttatttatgagatgggttttttatgattagagtcccgca attatacatttaatacgcgatagaaaacaaaatatagcgcgcaaactaggataaaattatcgcgcgcggtg tcatctatgttactagatcggg | | |
| GS<sub>NcoI</sub> F | 5'-TG<u>CCATGG</u>CTCATCTTTCGGATCTCGTT-3' | Forward primer for amplification of tobacco GS coding sequence, including restriction site for enzyme NcoI. | 8 |
| GS<sub>BstEII</sub> R | 5'-<u>GGGTGACCT</u>CAAGGCTCGGATAGGATAGTG -3' | Reverse primer for amplification of tobacco GS coding sequence, including restriction site for enzyme BstEII. | 9 |
| AspAT<sub>BgIII</sub> F | 5'-CAT<u>AGATCT</u>TATGGCTTCTCACGACAGCATCT -3' | Forward primer for amplification of Soyabean AspAT coding sequence, including restriction site for enzyme BgIII. | 10 |

-continued

| Name of the sequence | Sequence | Purpose | Sequence ID No. |
|---|---|---|---|
| AspAT<sub>PmlI</sub> R | 5'-GCCACGTGTTAGACAACTCGGGTTACAGCTG-3' | Reverse primer for amplification of Soyabean AspAT coding sequence, including restriction site for enzyme PmII. | 11 |
| PEP-Case<sub>BglII</sub> F | 5'-ATAGATCTTATGGCGTCGACCAAGGCTCCG -3' | Forward primer for amplification of maize PEPCase coding sequence, including restriction site for enzyme BgIII. | 12 |
| PEP-Case<sub>SpeI</sub> R | 5'-AGACTAGTGCCAGTGTTCTGCATGCCGGCGG3' | Reverse primer for amplification of maize PEPCase coding sequence, including restriction site for enzyme SpeI. | 13 |
| 35S<sub>SpeI</sub> F | 5'-GGACTAGTAATGGCGAATGCTAGAGCAGCTTGAG -3' | Forward primer for amplification of CaMV 35S promoter sequence, including restriction site for enzyme SpeI. | 14 |
| NosT<sub>AscI,BbvCI,PmlI</sub> R | 5'-GCCACGTGTCCTCAGCTGGCGCGCCCGCCAATATATCCTGTCAAACACTGATAGT-3' | Reverse primer for amplification of Nos terminator sequence, including | 15 |

-continued

| Name of the sequence | Sequence | Purpose | Sequence ID No. |
|---|---|---|---|
| | | restriction site for enzyme AscI, BbvCI PmlI | |
| NosT<sub>SpeI</sub> R | 5'-GG<u>ACTAGT</u>TTTAATTCCCGATC TAGTAACA TAGATG-3' | Reverse primer for amplification of Nos terminator sequence, including restriction site for enzyme SpeI. | 16 |
| 35G<sub>AscI</sub> F | 5'-ATCF<u>GGCGCGCC</u>AATGGCGAATGCTAGAGCAGCTTGAG -3' | Forward primer for amplification of CaMV 35S promoter sequence, including restriction site for enzyme AscI. | 17 |
| PEP-Case<sub>BbvCI</sub> R | 5'-GTG<u>CCTCAGCC</u>TAGCCAGTGTTCTGCATGCCGG -3' | Reverse primer for amplification of maize PEPCase coding sequence, including restriction site for enzyme BbvCI. | 18 |
| hpt F | 5'-GAGGGCGAAGAATCTCGTGC -3' | Forward primer for amplification of hygromycin phosphotransferase for screening transgenic plants. | 19 |
| hpt R | 5'-GATECTGGCGACCTCGTATTGG -3' | Reverse primer for amplification of hygromycin | 20 |

-continued

| Name of the sequence | Sequence | Purpose | Sequence ID No. |
|---|---|---|---|
| | | phosphotransferase for screening transgenic plants. | |
| PEPCase Exp F | 5'-ACGTCAGGAACTTCCAGGTIC-3' | Forward primer for maize PEPCase, used for RT-PCR based evaluation of PEPCase transgene expression. | 21 |
| PEPCase Exp R | 5'-CTTGTTCTCGTCGGCGAAC-3' | Reverse primer for maize PEPCase, used for RT-PCR based evaluation of PEPCase transgene expression. | 22 |
| GS Exp F | 5'-ACTTTCTGGACCTGTTGAT-3' | Forward primer for tobacco GS, used for RT-PCR based evaluation of GS transgene expression. | 23 |
| GS Exp R | 5'-GGCAGCACTGTGCCTT-3' | Reverse primer for tobacco GS, used for RT-PCR based evaluation of GS transgene expression. | 24 |
| AspAT Exp F | 5'-ATGGCTTCTCACGACAGCATC-3' | Forward primer for soyabean AspAT, used for RT-PCR based evaluation of GS transgene expression. | 25 |

| Name of the sequence | Sequence | Purpose | Sequence ID No. |
|---|---|---|---|
| AspAT Exp R | 5'-TTGCGTGACACGTCATTTATGAGT-3' | Reverse primer for soyabean AspAT, used for RT-PCR based evaluation of GS transgene expression. | 26 |
| 26S F | 5'-CACAATGATAGGAAGAGCCGAC-3' | Forward primer for 26SrRNA, used as internal control for RT-PCR based evaluation of transgene expression. | 27 |
| 26S R | 5'-CAAGGGAACGGGCTTGGCAGAATC-3' | Reverse primer for 26SrRNA, used as internal control for RT-PCR based evaluation of transgene expression | 28 |
| AspAT Pr | MASHDSISASPTSASDSVFNHLVRAPEDPILGVTVAYNKDPSPVKLNLGVGAYRTEEG KPLVLNVVRRVE QQLINDVSRNKEYIPIVGLADFNKLSAKLIFGADSPAIQDNRVTTVQCLSGTGSLRVGG EFLAKHYHQRT IYLPTPTWGNHPKVFNLAGLSVKTYRYYAPATRGLDFQGLLEDLGSAPSGSIVLLHACA HNPTGVDPTLE QWEQIRQLIRSKALLPFFDSAYQGFASGSLDADAQPVRLFVADGGELLVAQSYAKNLG LYGERVGALSIV CKSADVASRVESQLKLVIRPMYSSPPIHGASIVAAILKDRNLFNDWTIELKAMADRIISM RQELFDALCS RGTPGDWSHIIKQIGMFTFTGLNAEQVSFMTKEFHIYMTSDGRISMAGLSSKTVPLLA DAIHAAVTRVV | Represents Proteins of AspAT genes | 29 |
| GSPr | MAHLSDLVNLNLSDSTQKIIAEYIWIGGSGMDVRSKARTLSGPVDDPSKLPKWNYDG SSTGQAPGEDSEE ILYPQAIFKDPFRRGNNILVICDCYTPAGEPIPTNKRHSAAKIFSHPDVVVEEPWYGLEQ EYTLLQKDIN WPLGWPLGGFPGPQGPYYCGIGAGKVFGRDIVDSHYKACLYAGINISGINGEVMPGQ WEFQVGPSVGISA ADELWAARYILERITEIAGVVVSFDPKPIPGDWNGAGAHTNYSTKSMRNEGGYEVIKK AIENLGLRHKEH IAAYGEGNERRLTGRHETADINTFKWGVANRGASIRVGRDTEREGKGYFEDRRPASN MDPFVVTSMIAET TILSEP | Represents Proteins of GS genes | 30 |
| PEPCase Pr | MASTKAPGPGEKHHSIDAQLRQLVPGKVSEDDKLIEYDALLVDRFLNILQDLHGPSLRE FVQECYEVSAD YEGKGDTTKLGELGAKLTGLAPADAILVASSILHMLNLANLAEEVQIAHRRRNSKLKKG GFADEGSATTE | Represents Proteins of PEPCase genes | 31 |

| Name of the sequence | Sequence | Purpose | Sequence ID No. |
|---|---|---|---|
| | SDIEETLKRLVSEVGKSPEEVFEALKNQTVDLVFTAHPTQSARRSLLQKNARIRNCLTQL NAKDITDDDK QELDEALQREIQAAFRTDEIRRAQPTPQAEMRYGMSYIHETVWKGVPKFLRRVDTAL KNIGINERLPYNV SLIRFSSWMGGDRDGNPRVTPEVTRDVCLLARMMAANLYIDQIEELMFELSMWRCN DELRVRAEELHSSS GSKVTKYYIEFWKQIPPNEPYRVILGHVRDKLYNTRERARHLLASGVSEISAESSFTSIEE FLEPLELCY KSLCDCGDKAIADGSLLDLLRQVFTFGLSLVKLDIRQESERHTDVIDAITTHLGIGSYRE WPEDKRQEWL LSELRGKRPLLPPDLPQTDEIADVIGAFHVLAELPPDSFGPYIISMATAPSDVLAVELLQR ECGVRQPLP VVPLFERLADLQSAPASVERLFSVDWYMDRIKGKQQVMVGYSDSGKDAGRLSAAW QLYRAQEEMAQVAKR YGVKLTLFHGRGGTVGRGGGPTHLAILSQPPDTINGSIRVTVQGEVIEFCFGEEHLCFQ TLQRFTAATLE HGMHPPVSPKPEWRKLMDEMAVVATEEYRSVVVKEARFVEYFRSATPETEYGRMNI GSRPAKRRPGGGIT TLRAIPWIFSWTQTRFHLPVWLGVGAAFKFAIDKDVRNFQVLKEMYNEWPFFRVTLD LLEMVFAKGDPGI AGLYDELLVAEELKPFGKQLRDKYVETQQLLLQIAGHKDILEGDPFLKQGLVLRNPYITT LNVFQAYTLK RIRDPNFKVTPQPPLSKEFADENKPAGLVKLNPASEYPPGLEDTLILTMKGIAAGMQN TG | | |

Example 1

Amplification and Cloning of AspAT Gene

Nucleotide sequence encoding soybean cytosolic AspAT gene (SEQ ID NO: 1) was obtained from the NCBI database of nucleotide sequences (GenBank Accession No. AF034210.1; RNA from soybean plant was isolated using IRIS Plant RNA Kit (Ghawana et al., US Patent no 0344NF2004/IN). cDNA was synthesized using total RNA preparations (2 μg) in the presence of 1 μg oligo(dT)$_{12-18}$ and 400 U of reverse transcriptase Superscript II (Invitrogen) after digesting with 2 U DNase I (amplification grade, Invitrogen, USA) following the manufacturer's instructions. The full coding region of AspAT was then amplified from soybean cDNA using primers AspAT$_{BglII}$F (SEQ ID NO: 10) and AspAT$_{PmfI}$R (SEQ ID NO: 11) such that restriction sites BglII (AGATCT) and PmlI (CACGTG) is incorporated in the coding sequence for AspAT. Qiagen High Fidelity Taq polymerase enzyme was used for the PCR using the following conditions: initial denaturating at 94° C. for 3 minutes, 30 cycles of 94° C. for 30 seconds, annealing at 59° C. for 30 seconds, extension at 72° C. for 1 minute 20 seconds, with a final extension of 72° C. for 7 minutes. The amplification product was cloned in to pGEM®-T Easy Vector (cloning vector, Promega, USA). Plasmid from the positive clones and pCAMBIA 1302 plasmid were digested with BglII and PmlI and digested products isolated from an agarose gel electrophoresis were ligated and transformed in to E. coli DH5α cells which were obtained from Takara Bio Company, Japan (Cat. No. 9057). Plasmid from the positive colonies were sequenced to verify the in frame cloning of the AspAT coding sequence placed between CaMV 35S promoter (SEQ ID NO: 4) and Nos terminator (SEQ ID NO: 5) of pCAMBIA1302 and resulting vector was designated as AspAT::pCAMBIA1302.

Example 2

Amplification and Cloning of GS Gene

Nucleotide sequence encoding tobacco cytosolic GS gene (SEQ ID NO: 2) was obtained from the NCBI database of nucleotide sequences (GenBank Accession No. X95932.1. RNA from tobacco plant was isolated using iRIS Plant RNA Kit (Ghawana et al., US Patent no 0344NF2004/IN). cDNA was synthesized using total RNA preparations (2 μg) in the presence of 1 μg oligo(dT)$_{12-18}$ and 400 U of reverse transcriptase Superscript II (Invitrogen) after digesting with 2 U DNase I (amplification grade, Invitrogen, USA) following the manufacturer's instructions.

The full coding region of GS was amplified from tobacco cDNA using primers GS$_{NcoI}$ F with restriction sites NcoI (CCATGG) (SEQ ID NO: 8) and GS$_{BstEII}$ R with restriction sites for BstEII (GGTGACC) (SEQ ID NO: 9). GS$_{NcoI}$ F primers was modified so as to eliminate the BglII site by replacement of 'A' nucleotide by 'G' at position 15.

Qiagen High Fidelity Taq polymerase enzyme was used for the PCR using the following conditions: initial denaturating at 94° C. for 3 minutes, 30 cycles of 94° C. for 30 seconds, annealing at 59° C. for 30 seconds, extension at 72° C. for 1 minute 10 seconds, with a final extension of 72° C. for 7 minutes. The amplification product was cloned in to pGEM®-T Easy Vector (cloning vector, Promega, USA). Plasmids from the positive colonies and binary vector pCAMBIA 1302 were digested with NcoI and BstEII and digested product isolated from an agarose gel electrophoresis were ligated such that GS is placed downstream of CaMV 35S promoter of pCAMBIA vector. The ligation product was transformed in to E. coli DH5α cells and transformants were sequenced to verify the in frame cloning of the GS coding sequence and the resulting vector was designated as GS::pCAMBIA1302.

Example 3

Amplification and Cloning of Maize PEPCase Gene

Nucleotide sequence encoding maize PEPCase gene (SEQ ID NO: 3) was obtained from the NCBI database of nucleotide sequences (NCBI Reference Sequence: NM_001111948.1. RNA from maize plant was isolated using iRIS Plant RNA Kit (Ghawana et al., US Patent no 0344NF2004/IN). cDNA was synthesized using total RNA preparations (2 μg) in the presence of 1 μg oligo(dT)$_{12-18}$ and 400 U of reverse transcriptase Superscript II (Invitrogen) after digesting with 2 U DNase I (amplification grade, Invitrogen, USA) following the manufacturer's instructions.

The full coding region of PEPCase was amplified from maize cDNA using primers PEPCase$_{BgIII}$ F with restriction sites for BglII (AGATCT) (SEQ ID NO: 12) and PEPCase$_{SpeI}$ R with restricition sites for SpeI (ACTAGT) (SEQ ID NO: 13). Qiagen High Fidelity Taq polymerase enzyme supplemented with Q-solution (facilitating amplification of GC-rich templates) was used for PCR using the following conditions: initial denaturating at 94° C. for 3 minutes, 32 cycles of 94° C. for 30 seconds, annealing at 58° C. for 30 seconds, extension at 72° C. for 3 minute, with a final extension of 72° C. for 7 minutes. The amplification product was cloned in to pGEM®-T Easy Vector (cloning vector, Promega, USA). Plasmid from the positive clones and pCAMBIA 1302 plasmids were digested with BglII and SpeI and digested product isolated from an agarose gel electrophoresis were ligated and then transformed in to E. coli DH5α cells. Transformants were sequenced to verify the in frame cloning of the PEPCase coding sequence and resulting vector was designated as PEPCase::pCAMBIA 1302.

Example 4

Assembly of Expression Cassettes for AspAT, GS and PEPCase in Single pCAMBIA 1302 Vector (Generous Gift from "Centre for Application of Molecular Biology to International Agriculture", Australia)

A stepwise method for amplification and integration of expression cassettes each for AspAT, GS and PEPCase in to single plant transformation vector pCAMBIA 1302 is described as follows:

GS expression cassette comprising CaMV35S promoter, downstream cloned GS and nopaline synthase (hereinafter, referred as "Nos") terminator was amplified from GS:: pCAMBIA 1302 vector (Example 2), using primers 35$_{SpeI}$F (SEQ ID NO: 14) and NosT$_{AscI, BbvCI, PmlI}$ R (SEQ ID NO: 15). The primers were designed to incorporate the SpeI (ACTAGT) in the forward primer and AscI (GGCGCGCC), BbvCI (CCTCAGC) and PmlI (CACGTG) in reverse primer to facilitate the subcloning of GS expression cassette in to SpeI and PmlI sites of pCAMBIA 1302 vector as well as to create the additional restriction sites (AscI, BbvCI) at 3' end in the vector backbone. Qiagen High Fidelity Taq polymerase enzyme was used for the PCR using the following conditions: initial denaturating at 94° C. for 3 minutes, 30 cycles of 94° C. for 30 seconds, annealing at 59° C. for 30 seconds, extension at 72° C. for 2 minutes, with a final extension of 72° C. for 7 minutes. The amplification product was cloned in to p®GEM-T Easy Vector (cloning vector, Promega, USA). Plasmids from the positive clones was digested with SpeI and PmlI, and the digested product was then isolated from an agarose gel electrophoresis and ligated in to SpeI and PmlI sites of pCAMBIA 1302 vector. The ligation product was transformed in to E. coli DH5α cells and transformants were verified by sequencing of plasmid.

AspAT coding sequence along with 3'Nos terminator sequence was amplified from AspAT:: pCAMBIA 1302 vector (Example 1) using primers AspAT$_{BgIII}$ F (SEQ ID NO: 10) and NosT$_{SpeI}$ (SEQ ID NO: 16) with restriction sites for BglII (AGATCT) and SpeI (ACTAGT) respectively.

Qiagen High Fidelity Taq polymerase enzyme was used for the PCR using the following conditions: initial denaturation at 94° C. for 3 minutes, 30 cycles of 94° C. for 30 seconds, annealing at 59° C. for 30 seconds, extension at 72° C. for 2 minutes, with a final extension of 72° C. for 7 minutes. The amplification product was cloned in to pGEM®-T Easy Vector (cloning vector, Promega, USA). Plasmids from the positive clones upon digestion with BglII and SpeI, cloned downstream of CaMV 35S promoter of destination pCAMBIA 1302 (previously cloned with GS expression cassette). The ligation product was then transformed in to E. coli DH5α cells and transformants were sequenced to verify the in frame cloning of the AspAT coding sequence.

CaMV 35S promoter along with the downstream cloned PEPCase gene from PEPCase:: pCAMBIA 1302 vector (example 3) was amplified with the primers 35S$_{AscI}$ F (SEQ ID NO: 17) having restriction site for AscI (GGCGCGCC) and PEPCase$_{BBvCI}$ R (SEQ ID NO: 18) having restriction site for BbVCI (CCTCAGC).

Qiagen High Fidelity Taq polymerase enzyme was used for the PCR using the following conditions: initial denaturation at 94° C. for 3 minutes, 30 cycles of 94° C. for 30 seconds, annealing at 60° C. for 30 seconds, extension at 72° C. for 4 minutes, with a final extension of 72° C. for 7 minutes. The amplification product was cloned in to pGEM®-T Easy Vector (cloning vector, Promega, USA), plasmid from the positive clones was digested with AscI (GGCGCGCC) and BbVCI (CCTCAGC) and digested product isolated from an agarose gel electrophoresis ligated upstream of Nos terminator sequence of destination pCAMBIA 1302 previously cloned with GS and AspAT expression cassettes. The ligation product was transformed in to E. coli DH5α cells and transformants sequenced to verify the in frame cloning of the PEPCase coding sequence. Resultant plant expression vector was designated as AspAT+GS+PEPCase for co-overexpression of AspAT, GS and PEPcase. A hygromycin resistance gene (SEQ ID NO. 6) was included as a selectable marker for screening transgenic plants. Schematic diagram of expression construct is shown in FIG. 1, represented by SEQ ID NO. 7 for plant transformation such that the transgenic plant produces higher amount of proteins represented by SED ID NO. 29, 30, and 31.

Example 5

Raising of Transgenic Arabidopsis Plants Co-Over Expressing Genes AspAT, GS and PEPCase Generation of Plant Expression Vector (AspAT+GS+PEPCase)

Briefly, the plant expression vector was constructed as follows: cDNA sequences encoding soybean AspAT gene (SEQ ID NO: 1), tobacco cytosolic GS gene (SEQ ID NO: 2) and maize PEPCase gene (SEQ ID NO: 3), were first independently cloned in to pCAMBIA 1302 vector. The elements for expression cassette for AspAT, GS and PEP- Case were then amplified and assembled in to destination pCAMBIA1302 such that genes AspAT, GS and PEPCase were controlled by independent CaMV 35S promoter and Nos transcriptional terminator.

Agrobacterium Mediated Plant Transformation:

AspAT+GS+PEPCase were transferred to *Agrobacterium tumefaciens* strain GV3101 with ATCC number *Agrobacterium tumefaciens* (GV3101 (pMP90RK) (C58 derivative) ATCC® Number: 33970 Reference: Hayashi H, Czaja I, Lubenow H, Schell J, Walden R. 1992 using standard triparental mating method.

Briefly, *E. coli* DH5α cells harboring the recombinant construct AspAT+GS+PEPCase and those harboring helper plasmid pRK2013 were cultured overnight at 37° C. *Agrobacterium* strain GV3101 grown at 28° C. for 48 hrs. All the three cultures were then pelleted, washed, and mixed, followed by plating on YEM (Yeast Extract Mannitol) plates supplemented with the antibiotics kanamycin (50 ug/ml) and rifampcin (50 ug/ml). Antibiotic resistant colonies were verified by colony PCR to assure the transformation of *Agrobacterium* with the recombinant construct AspAT+GS+PEPCase.

*Arabidopsis* Seeds of the Columbia Ecotype were Generous Gift by Dr. Christine H Foyer Of, IACR-Rothamsted, Harpenden, UK

*Arabidopsis* plants were transformed with *Agrobacteria* harboring AspAT+GS+PEPCase using vacuum infiltration method. Briefly, liquid 5-ml cultures were established from single transformed *Agrobacterium* colony and grown in YEM medium supplemented with 50 ug/ml kanamycin, 50 ug/ml rifampicin at 28° C. up to the late logarithmic phase. Next, 1 ml of bacterial suspension was diluted with 100 ml of YEB culture medium supplemented with the same antibiotics. The culture was grown overnight until their optical density reached 1.2-1.8 at 600 nm. The bacteria were spinned for 20 min at 2000 g at room temperature and suspended in a solution for infiltration containing half strength MS (Murashige and Skoog) medium with 2% sucrose, 0.05% MES (Sigma,) and 0.01% of Silwet L-77 (Lehle Seeds, United States). *Arabidopsis* inflorescences were dipped in bacterial suspension and infiltrated under vacuum for 10 minutes. Plants were then transferred to growth chamber and grown under controlled long day conditions (16-h light at 22-23° C. and 8-h darkness at 20° C.) for seed set.

Selection of Primary Transformant $T_o$ Transgenic *Arabidopsis* Plant:

Seeds from transformed plants were surface sterilized by immersion in 70% (v/v) ethanol for 2 min, followed by immersion in 10% (v/v) sodium hypochlorite solution. Seeds were then washed four times with sterile distilled water and sown onto 1% agar containing MS medium supplemented with hygromycin B at a concentration of 20 µml$^{-1}$ (Sigma # H3274). Seeds were then stratified for 2 days in the dark at 4° C. After stratification plates were transferred to a growth chamber with 16 h light and 8 h dark cycle for germination. After 14-days, hygromycin resistant seedlings were selected as putative primary transformants ($T_0$) and transferred to pots containing vermiculite, perlite and cocopeat mix (1:1:1) and grown to maturity under controlled condition of light, temperature and humidity for growth and seed set.

Raising T1 and $T_2$ Generation AspAT+GS+PEPCase Transgenic Plants:

Seeds harvested from $T_0$ transgenic plants were germinated on MS+hygromycin B (at a concentration of 20 µml$^{-1}$) plates and transgenic lines exhibiting a segregation ratio of 3:1 (scored by their sensitivity to hygromycin B) were selected to raise T1 generation of transgenic plants. Homozygous transgenic plants were obtained in the $T_2$ generation and evaluated for different physiological and biochemical parameters in comparison to wild control plants.

Example 6

Analysis of the Genomic DNA from *Arabidopsis thaliana* Plants Transformed with AspAT+CS+PEPCase

*Arabidopsis* plants from two independent transgenic lines transformed with AspAT+GS+PEPCase were selected to verify the insertion of transgenes in to plant genome. The genomic DNA was isolated using DNeasy Plant mini kit (QIAGEN Co.). PCR was carried out by using the isolated DNA as template with primers hpt F (SEQ ID NO: 19) and hpt R (SEQ ID NO: 20) annealing to the hygromycin phosphtransferaes (hpt) gene (SEQ ID NO: 6) (plant selection marker from pCAMBIA 1302 vector).

PCR cycling conditions defined by initial denaturation at 94° C. for 3 minutes, 28 cycles of 94° C. for 30 seconds, annealing at 58° C. for 30 seconds, extension at 72° C. for 1 minute, with a final extension of 72° C. for 7 minutes.

Figure 2:
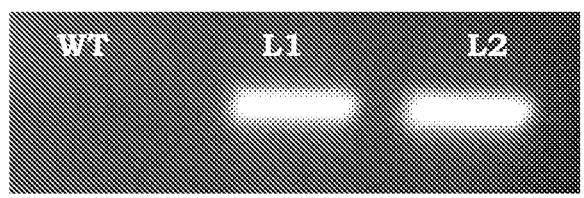
FIG. 2 represents DNA analysis (a) and RNA analysis (b) of WT, L1 and L2, where WT=wild; L1 and L2=two different transgenic lines co-overexpressing AspAT, GS and PEPCase.
Figure 2:
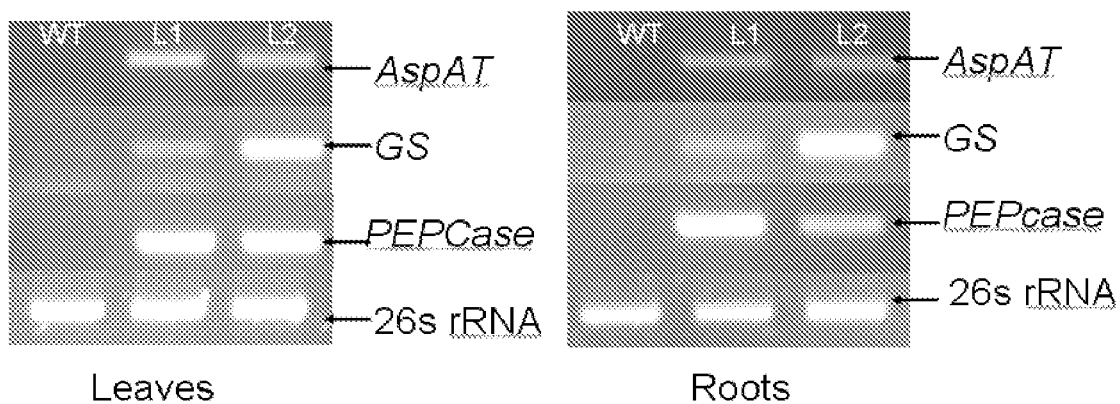

The result is shown in FIG. 2A, in which WT represents the wild and L1 and L2 represent two different transgenic lines. The amplification of hpt gene was observed only with transgenic confirming insertion of AspAT+GS+PEPCase in to *Arabidopsis* plants.

Example 7

Evaluation of AspAT+GS+PEPCase Transgenics by Reverse Transcriptase—Polymerase Chain Reaction (RT-PCR)

RNA analysis of transformants was done to confirm the expression of AspAT, GS and PEPCase. Total RNA was isolated from leaf and root of transgenic plants using iRIS Plant RNA Kit (Ghawana et al., US Patent no 0344NF2004/IN). cDNA was synthesized using total RNA preparations (2 µg) in the presence of 1 µg oligo(dT)$_{12-18}$ and 400 U of reverse transcriptase Superscript II (Invitrogen) after digesting with 2 U DNase I (amplification grade, Invitrogen, USA) following the manufacturer's instructions). Expression of transgenes was evaluated using gene specific primer for AspAT, GS and PEPCase, designated as PEPCase Exp F (SEQ ID NO: 21), PEPCase Exp R (SEQ ID NO: 22), GS Exp F (SEQ ID NO: 23), GS Exp R (SEQ ID NO: 24), AspAT Exp F (SEQ ID NO: 25) and AspAT ExpR (SEQ ID NO: 26). As a positive control for RT-PCR, 26S rRNA was amplified using primers 26S F (SEQ ID NO: 27) and 26S R (SEQ ID NO: 28).

The results of analyses are shown in FIG. 2B, in which WT represents wild and L1 and L2 represent two transgenic lines. The amplification of RT-PCR products were observed only in trangenics confirming the expression of introduced genes.

Example 8

Enzymatic Assays from Wild Type and AspAT+GS+PEPCase Transgenic *Arabidopsis* Plants Enzymatic assays were performed with AspAT+GS+PEPCase transgenic and wild plants as follows:

PEPCase Activity Measurement: Frozen leaf samples (200 mg) ground with a mortar and pestle in 1 ml of extraction buffer containing 50 mM Tris-Cl buffer (pH 7.5), 1.0 mM $MgCl_2$, 5.0 mM DTT, 1.0 mM PMSF, 2% (w/v) PVPP, 10% (v/v) glycerol and 0.1% (v/v) Triton X-100. The extract was centrifuged at 12,000 g for 10 min at 4° C. and the supernatant was used for the determination of enzyme activity. PEPCase was assayed spectrophotometrically at 340 nm in the presence of excess MDH and lactate dehydrogenase (Ashton et al. 1990). The reaction mixture contained 50 mM Tris-Cl (pH 8.0), 5 mM $MgCl_2$, 5 mM DTT, 1 mM $NaHCO_3$, 5 mM glucose-6-phosphate, 0.2 mM NADH, 2 units MDH, 0.1 units lactate dehydrogenase and crude extract. The reaction was initiated by the addition of 5 mM PEP.

AspAT Activity Measurement: Extraction buffer for AspAT consisted of 200 mM Tris-Cl buffer (pH 7.5), 2.0 mM EDTA and 20% glycerol.

The enzyme was assayed in an MDH-coupled reaction essentially as described by Ireland and Joy (1990). Briefly the reaction mixture contained 10 mM 2-oxoglutarate, 2 mM aspartate, 0.2 mM NADH, and 50 mM HEPES buffer (pH 8.0). Reaction was started by addition of 2-oxoglutarate. Assay control was run by excluding the 2-oxoglutarate from the reaction mix.

GS Activity Measurement:

GS (glutamine synthetase) was extracted in the grinding medium containing 50 mM Tris-Cl buffer (pH 7.8), 1 mM EDTA, 10 mM $MgSO_4$, 5 mM sodium glutamate, 10% (v/v) glycerol and insoluble PVPP (2% w/v). Enzyme assay was performed as described earlier by Lea et al. (1990) and the activity was calculated from the standard curve prepared with γ-glutamylhydroxamate.

Figure 5:
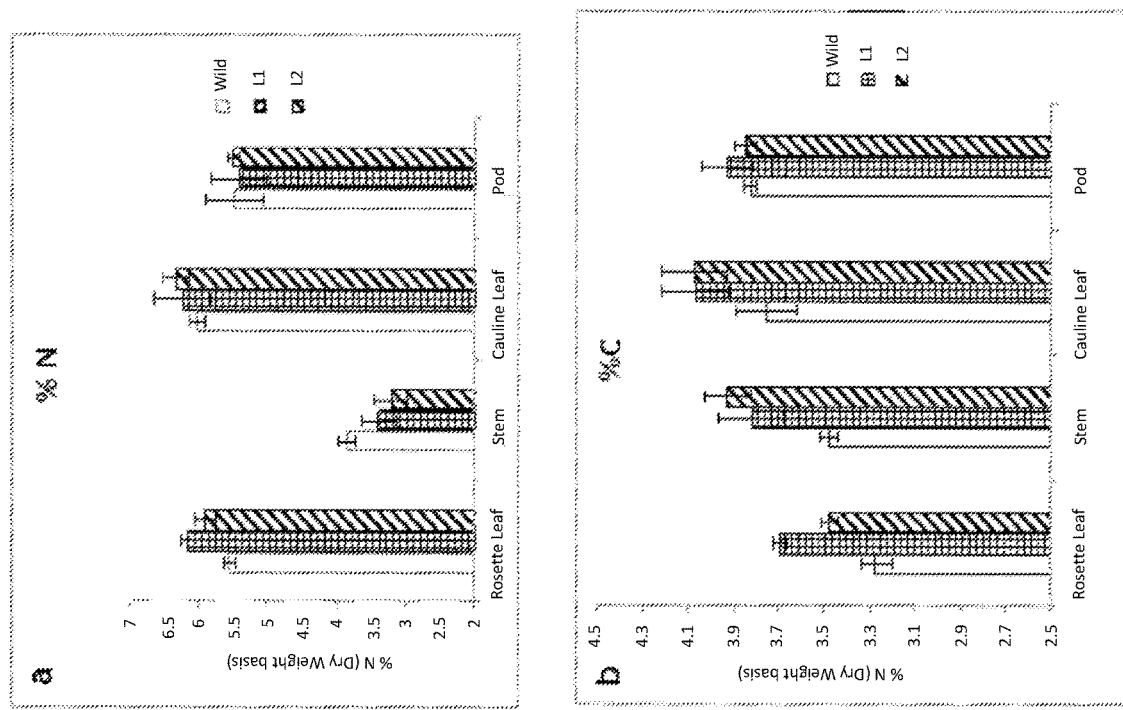
FIG. 5 represents Analyses of N (a) and C (b) content from different plant parts of WT, L1 and L2 lines at 65 days of sowing. Data is mean of three separate biological replicates with standard deviation marked on each bar.

The results of the analyses are shown in the FIG. 5A to 5C, an increase of about 45 to 50% in PEPCase activity, 55% in GS activity and 55 to 60% in AspAT activity was observed with two independent AspAT+GS+PEPCase transgenic plants compared to wild plants.

Example 9

C and N Analyses in Wild and AspAT+GS+PEPCase Transgenic Arabidopsis Plants

Figure 6:
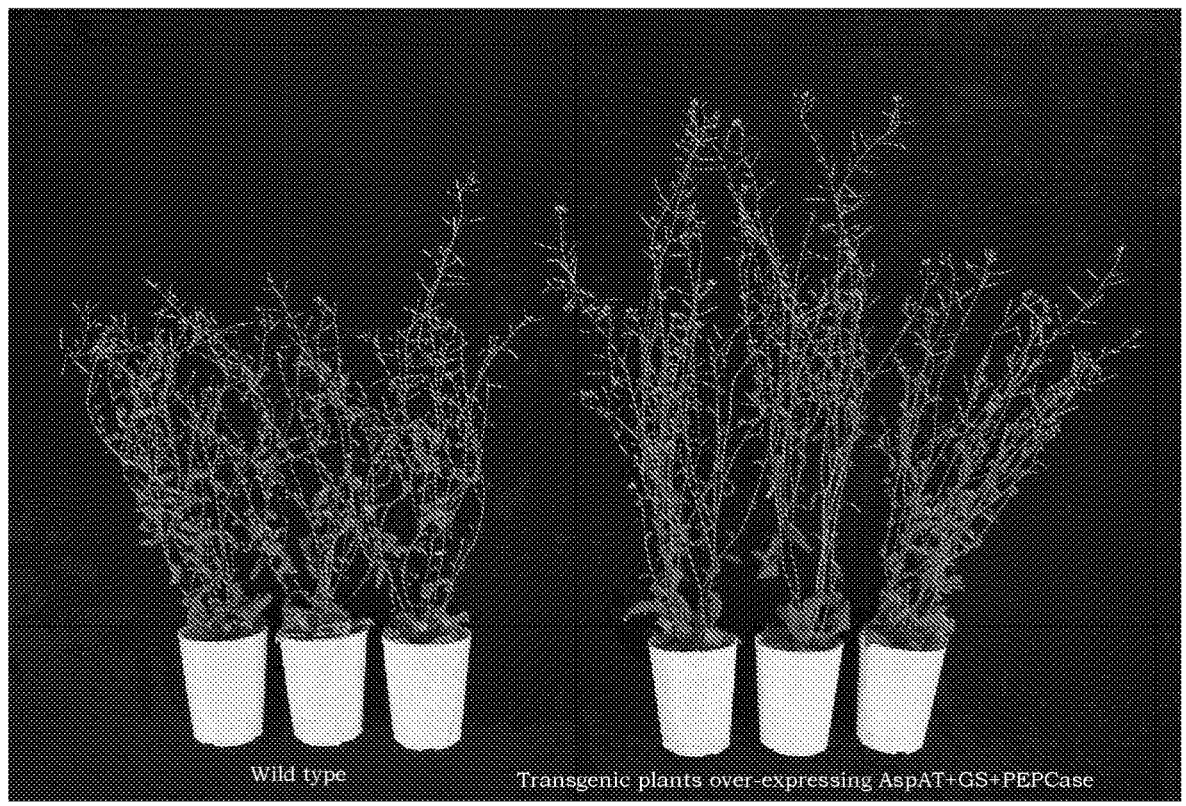
FIG. 6 represents a representative WT and AspAT+GS+PEPCase transgenic plants at 75 days of sowing.

Seeds of AspAT+GS+PEPCase transformed Arabiopdsis thaliana plants and wild control plants were germinated on half strength MS plates supplemented with 20 g/l sucrose. 14 days-old seedlings were transferred to pots containing mix of vermiculite; perlite and coco peat in the ratio of 1:1:1 and grown under long-day conditions comprising 16 hours of light period at 22° C. and 8 hours of dark period at 20° C. maintained in the Arabidopsis growth chamber. Different plant parts including rosette leaf; stem, cauline leaf and green pods were harvested from 65-days old plants and dried at 80° C. for 48 hrs. The quantitative determination of the C and N elements was conducted with Elementar CHNS analyzer using sulfanilamide as standard. The results are shown in FIG. 6. The elementary analysis showed that the total C and N content in AspAT+GS+PEPCase transgenic plant leaves has significantly increased by co-overexpression of AspAT, GS and PEPCase compared to wild plants.

Example 10

Figure 3:
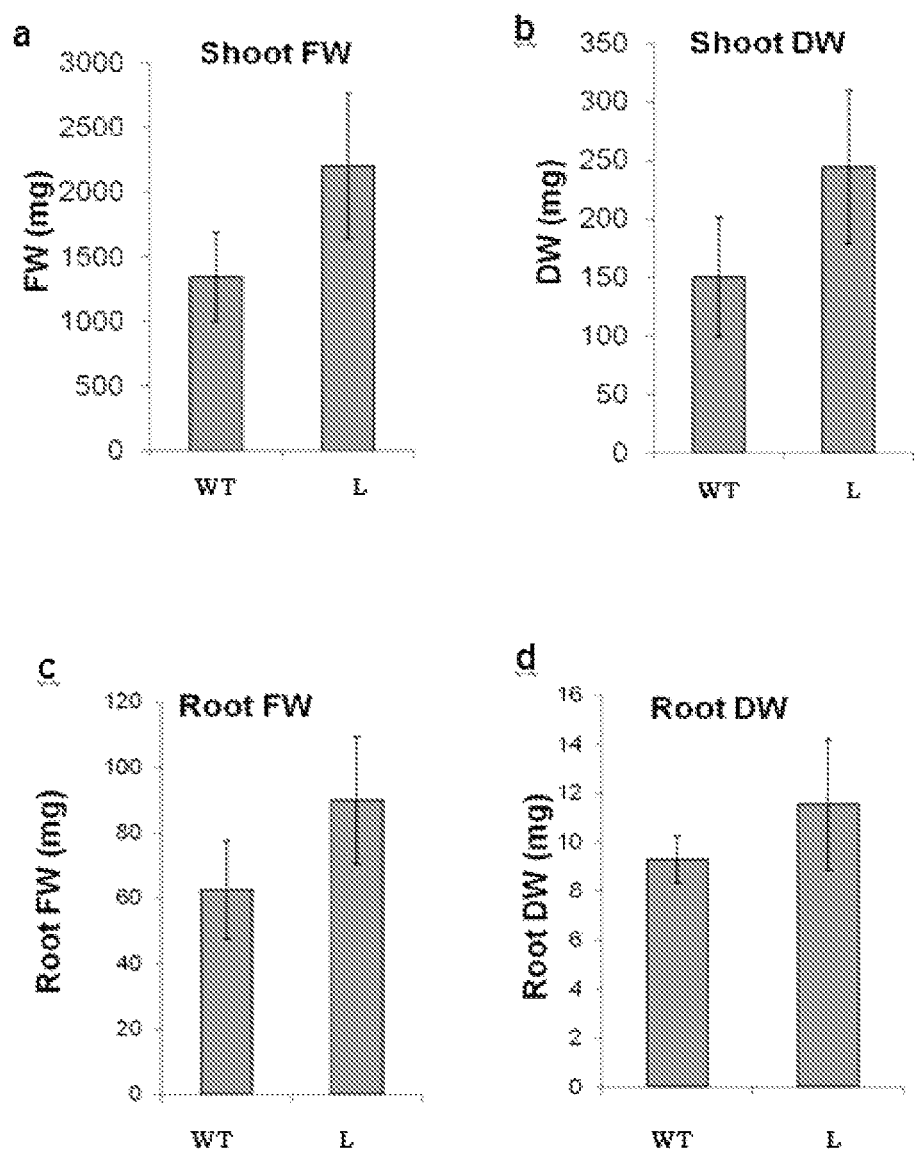
FIG. 3 represents shoot fresh weight (FW) (a), shoot dry weight (DW) (b), root fresh weight (c) and root dry weight (d) of WT and AspAT+GS+PEPCase transgenic plants at 60 days of sowing. Data is mean of five separate biological replicates with standard deviation marked on each bar.
Figure 4:
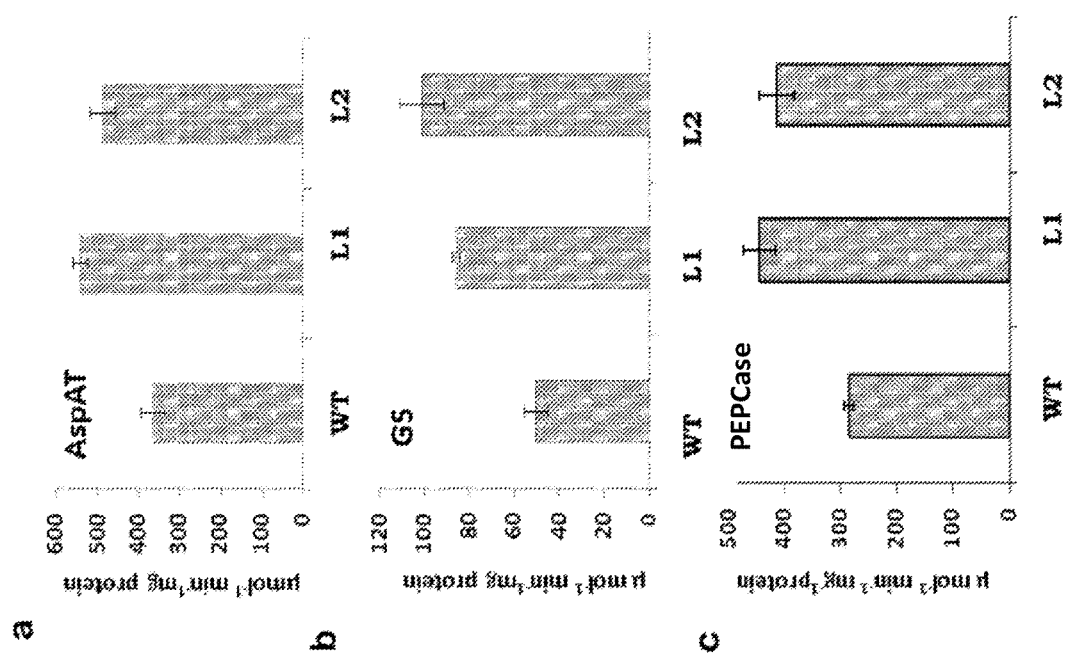
FIG. 4 represents AspAT activity (a) GS activity (b) and PEPCase activity (d) of WT, L1 and L2 at 42 days of sowing. Data is mean of three separate biological replicates with standard deviation marked on each bar.

Investigation of Growth and Yield in Wild and AspAT+GS+PEPCase Transgenic Plants Wild and AspAT+GS+PEPCase transgenic plants were analyzed for different growth characteristics. Shoot, root fresh and dry weight was recorded for 60-days old plants. Across different parameters evaluated, AspAT+GS+PEPCase plants showed enhanced growth characteristics. In particular, the transgenic plants have more number of leaves per rosette having larger area. Transgenic plants exhibited about 70% increase in the shoot fresh weight with 60% increase in the shoot dry weight whereas the increase of about 40% and 30% was observed in the root fresh and dry weight respectively (shown in FIG. 3).

Figure 7:
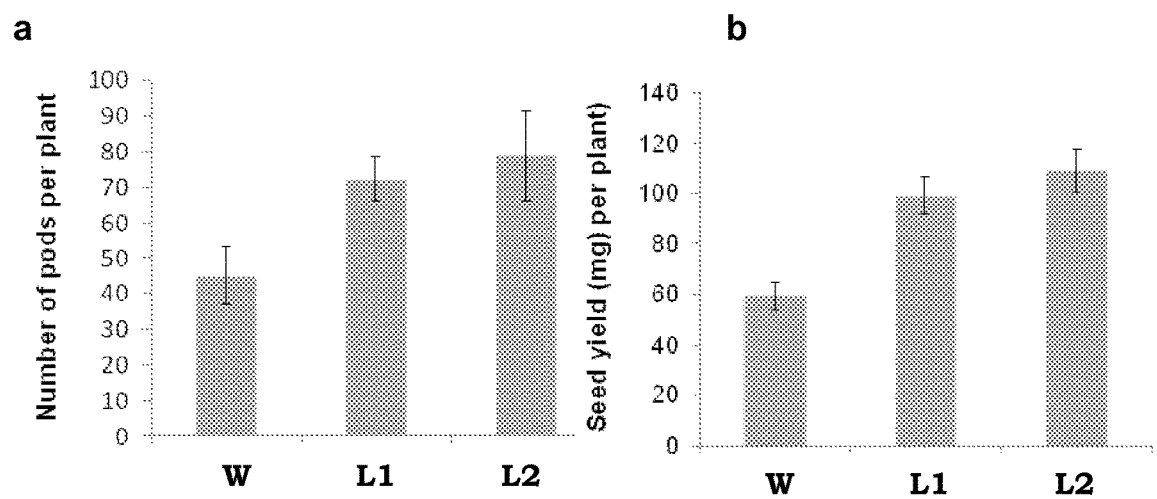
FIG. 7 represents pod number (a) and seed yield (b) in WT, L1 and L2 at 75 days of sowing. Data is mean of five separate biological replicated with standard deviation marked on each bar.

Total number of pods from 72-days old AspAT+GS+PEPCase transgenic plants was calculated and compared to untransformed wild plants (shown in FIG. 7 a). Furthermore total seed yield (total seed weight per plant) was also measured for transgenic and control plants. Across both the parameters, AspAT+GS+PEPCase transgenic Arabidopsis plant showed increase in yield compared to wild plants as shown in FIG. 7 b.

ADVANTAGES OF THE INVENTION

1. There have been efforts to enhance carbon and nitrogen status of plants, a step towards food security.
2. The present invention provides an innovative approach wherein overexpression of PEPCase provides a carbon skeleton to capture nitrogen assimilated through over expression of AspAT and GS.
3. The improved capacity of plant for carbon and nitrogen capture was also reflected in improved plant productivity both in terms of plant seed and plant biomass production.

The invention claimed is:

1. An expression construct set forth in SEQ ID NO. 7 that encodes and co-overexpresses a set limited to three heterologous plant enzymes, the enzymes consisting of a soybean aspartate aminotransferase (AspAT) according to amino acid sequence SEQ ID NO:29, a tobacco cytosolic glutamine synthetase (GS) according to amino acid sequence SEQ ID NO:30, and a maize phosphoenolpyruvate carboxylase (PEPCase) according to amino acid sequence SEQ ID NO:31 when transformed into a plant to form a transgenic plant, the overexpression of the three heterologous enzymes resulting in enhanced biomass and increased seed and/or pod yield in the transgenic plant as compared to a wildtype or untransformed plant.

2. A transgenic plant comprising the expression construct as claimed in claim 1.

3. A process for enhancing the number of seed pods and/or seed yield in a plant, wherein the process comprises the steps of:
   a) transforming an *Agrobacterium tumefacians* strain with the expression construct as claimed in claim 1;
   b) transforming explants with the recombinant *Agrobacterium tumefacians* strain as obtained in step (a); and
   c) selecting the transformed explants of step (b) to obtain the desired transformed plants having an enhanced number of seed pods and/or seed yield in a plant as compared to a wild type plant.

4. A process as claimed in claim 3, wherein the explants are selected from the group comprising of *Arabidopsis*, tomato, potato, tobacco, maize, wheat, rice, cotton, mustard, pigeon pea, cowpea, pea, sugarcane, soyabean and sorghum.

5. An expression construct, as claimed in claim 1, for co-overexpression of three heterologous plant enzymes in a plant, the construct comprising:

from 5' to 3', a nucleic acid encoding a constitutive promoter linked to a nucleic acid encoding a soybean asparate aminotransferase (AspAT) linked to a nucleic acid encoding a terminator;

from 5' to 3', a nucleic acid encoding a constitutive promotor linked to a nucleic acid encoding a tobacco cytosolic glutamine synthetase (GS) linked to a nucleic acid encoding a terminator; and from 5' to 3', a nucleic acid encoding a constitutive promotor linked to a nucleic acid encoding a maize phosphoenolpyruvate carboxylase (PEPCase) linked to a nucleic acid encoding a terminator;

wherein, the AspAT, GS and PEPCase are the only plant enzymes encoded by the expression construct, and wherein, when introduced into a plant cell, the expression construct provides for co-overexpression of the AspAT, GS, and PEPCase and results in enhanced biomass and yield compared to wild-type plants.

6. A plant comprising the expression construct as claimed in claim 5.

7. A process for enhancing the number of seed pods and/or seed yield in a plant, wherein the process comprises the steps of:
   a) transforming explants with a recombinant *Agrobacterium tumefacians* strain transformed with the expression construct of claim 5; and
   b) selecting the transformed explants of step (a) to obtain transformed plants having an enhanced number of seed pods and/or seed yield in a plant as compared to a wild type plant.

* * * * *

SEQUENCE LISTING

```
<160> NUMBER OF SEQ ID NOS: 31

<210> SEQ ID NO 1
<211> LENGTH: 1260
<212> TYPE: DNA
<213> ORGANISM: Artificial Sequence
<220> FEATURE:
<223> OTHER INFORMATION: Glycine max AspAT cDNA sequence

<400> SEQUENCE: 1
atggcttctc acgacagcat ctccgcttct ccaacctccg cttctgattc cgtcttcaat      60
cacctcgttc gtgctcccga agatcctatc ctcggggtaa ctgtcgctta taacaaagat     120
ccaagtccag ttaagctcaa cttgggagtt ggtgcttacc gaactgagga aggaaaacct     180
```

```
cttgttttga atgtagtgag gcgagttgaa cagcaactca taaatgacgt gtcacgcaac      240
aaggaatata ttccgatcgt tgggcttgct gattttaata aattgagtgc taagcttatt      300
tttggggctg acagccctgc tattcaagac aacagggtta ccactgttca atgcttgtct      360
ggaactggtt ctttaagagt tgggggtgaa ttttttggcta acactatca ccaacggact      420 atatacttgc caacaccaac ttggggcaat cacccgaagg ttttcaactt agcaggcttg      480
tctgtcaaaa cataccgcta ctatgctcca gcaacacgag gacttgactt tcaaggactt      540
ctggaagacc ttggttctgc tccatctgga tctattgttt tgctacatgc atgcgcacat      600
aaccccactg gtgtggatcc aacccttgag caatgggagc agattaggca gctaataaga      660
tcaaaagctt tgttaccttt ctttgacagt gcttatcagg gttttgctag tggaagtcta      720
gatgcagatg cccaacctgt tcgtttgttt gttgctgatg gaggcgaatt gctggtagca      780
caaagctatg caaagaatct gggtctttat ggggaacgtg ttggcgcctt aagcattgtc      840
tgcaagtcag ctgatgttgc aagcaggggtt gagagccagc tgaagctagt gattaggccc      900
atgtactcaa gtcctcccat tcatggtgca tccattgtgg ctgccattct caaggaccgg      960
aatttgttca atgactggac tattgagttg aaggcaatgg ctgatcgcat catcagtatg     1020
cgccaagaac ttttcgatgc tttatgttcc agaggcacac ctggcgattg gagtcacatt     1080
atcaaacaga ttggaatgtt tactttcact ggattgaatg cggaacaagt ttccttcatg     1140
actaaagagt tccatatata catgacatct gatggggagga ttagcatggc tggtctgagt     1200
tccaaaactg tcccacttct ggcggatgcg atacatgcag ctgtaacccg agttgtctaa     1260
```

<210> SEQ ID NO 2
<211> LENGTH: 1071
<212> TYPE: DNA
<213> ORGANISM: Artificial Sequence
<220> FEATURE:
<223> OTHER INFORMATION: Nicotiana tabacum GS cDNA sequence

<400> SEQUENCE: 2

```
atggctcatc tttcagatct cgttaatctc aatctctctg actccactca gaaaattatt       60
gctgaataca tatggattgg tggatcagga atggacgtca ggagcaaagc cagaacactt      120
tctggacctg ttgatgatcc ttcaaagctt cccaaatgga attatgatgg ttctagcaca      180
ggacaagctc ctggagaaga cagtgaagag atcctatatc tcaagcaat tttcaaggat      240 ccattcagaa ggggcaacaa tatcttggtc atttgtgatt gttacacccc agctggtgaa      300
cccattccaa caaacaaaag gcacagtgct gccaagattt cagccaccc tgatgttgtt      360 gttgaggaac cctggtatgg tcttgagcaa gaatacacct tgttgcaaaa agatatcaat      420
tggcctcttg gatggcctct tggtggtttt cctggaccac agggaccata ctattgcgga      480
attggagctg gaaaggtctt tggacgcgat atcgttgact tcattataa ggcatgtctc      540 tatgctggga ttaacatcag tggtatcaat ggagaagtga tgcccggaca gtgggaattt      600
caagttggac cttcagttgg catttcagca gctgatgaat tgtgggcagc tcgttacatt      660
cttgagagga ttactgagat tgctggagtt gtggtctcat tgacccccaa acctattccg      720
ggtgactgga tggtgctgg agctcacaca aactacagca caaagtctat gaggaatgaa      780
ggaggctatg aagtcattaa gaaggcaatt gagaacctttg gactgaggca caaggagcat      840
attgcagcat atggtgaagg caacgagcgt cgtctcactg gaagacacga aacagctgac      900
atcaacacat tcaaatgggg agttgcgaac cgtggtgcat ctattcgtgt gggaagagac      960
```

```
acggagagag aagggaaggg atacttcgag gataggaggc ctgcttcgaa tatggatcca      1020
ttcgtcgtga cttccatgat tgctgagacc actatcctat ccgagccttg a              1071

<210> SEQ ID NO 3
<211> LENGTH: 2913
<212> TYPE: DNA
<213> ORGANISM: Artificial Sequence
<220> FEATURE:
<223> OTHER INFORMATION: Zea mays PEPCase cDNA sequence

<400> SEQUENCE: 3
atggcgtcga ccaaggctcc cggccccggc gagaagcacc actccatcga cgcgcagctc        60
cgtcagctgg tcccaggcaa ggtctccgag gacgacaagc tcatcgagta cgatgcgctg       120
ctcgtcgacc gcttcctcaa catcctccag gacctccacg gcccagcct  tcgcgaattt       180 gtccaggagt gctacgaggt ctcagccgac tacgagggca aggagacac  gacgaagctg       240 ggcgagctcg cgccaagct  cacggggctg gccccgccg  acgccatcct cgtggcgagc       300
tccatcctgc acatgctcaa cctcgccaac ctggccgagg aggtgcagat cgcgcaccgc       360
cgccgcaaca gcaagctcaa gaaaggtggg ttcgccgacg agggctccgc caccaccgag       420
tccgacatcg aggagacgct caagcgcctc gtgtccgagg tcggcaagtc ccccgaggag       480
gtgttcgagg cgctcaagaa ccagaccgtc gacctcgtct tcaccgcgca tcctacgcag       540
tccgcccgcc gctcgctcct gcaaaaaaat gccaggatcc gaaattgtct gacccagctg       600
aatgccaagg acatcactga cgacgacaag caggagctcg atgaggctct gcagagagag       660
atccaagcag ccttcagaac cgatgaaatc aggagggcac aacccacccc gcaggccgaa       720
atgcgctatg ggatgagcta catccatgag actgtatgga agggtgtgcc taagttcttg       780
cgccgtgtgg atacagccct gaagaatatc ggcatcaatg agcgccttcc ctacaatgtt       840
tctctcattc ggttctcttc ttggatgggt ggtgaccgcg atggaaatcc aagagttacc       900
ccggaggtga caagagatgt atgcttgctg ccagaatgat ggctgcaaa  cttgtacatc       960 gatcagattg aagagctgat gtttgagctc tctatgtggc gctgcaacga tgagcttcgt      1020
gttcgtgccg aagagctcca cagttcgtct ggttccaaag ttaccaagta ttacatagaa      1080
ttctggaagc aaattcctcc aaacgagccc taccgggtga tactaggcca tgtaagggac      1140
aagctgtaca cacacgcga  gcgtgctcgc catctgctgg cttctggagt ttctgaaatt      1200
tcagcggaat cgtcatttac cagtatcgaa gagttccttg agccacttga gctgtgctac      1260
aaatcactgt gtgactgcgg cgacaaggcc atcgcggacg ggagcctcct ggacctcctg      1320
cgccaggtgt tcacgttcgg gctctccctg gtgaagctgg acatccggca ggagtcggag      1380
cggcacaccg acgtgatcga cgccatcacc acgcacctcg gcatcgggtc gtaccgcgag      1440
tggcccgagg acaagaggca ggagtggctg ctgtcggagc tgcgaggcaa gcgcccgctg      1500 ctgccccgg  accttcccca gaccgacgag atcgccgacg tcatcggcgc gttccacgtc      1560
ctcgcggagc tcccgcccga cagcttcggc ccctacatca tctccatggc gacggcccc      1620 tcggacgtgc tcgccgtgga gctcctgcag cgcgagtgcg gcgtgcgcca gccgctgccc      1680
gtggtgccgc tgttcgagag gctggccgac ctgcagtcgg cgcccgcgtc cgtggagcgc      1740
ctcttctcgg tggactggta catggaccgg atcaagggca agcagcaggt catggtcggc      1800
tactccgact ccggcaagga cgccggccgc ctgtccgcgg cgtggcagct gtacagggcg      1860
caggaggaga tggcgcaggt ggccaagcgc tacggcgtca agctcacctt gttccacggc      1920
cgcggaggca ccgtgggcag gggtggcggg cccacgcacc ttgccatcct gtcccagccg      1980
```

```
ccggacacca tcaacgggtc catccgtgtg acggtgcagg gcgaggtcat cgagttctgc    2040
ttcggggagg agcacctgtg cttccagact ctgcagcgct tcacggccgc cacgctggag    2100
cacggcatgc acccgccggt ctctcccaag cccgagtggc gcaagctcat ggacgagatg    2160
gcggtcgtgg ccacggagga gtaccgctcc gtcgtcgtca aggaggcgcg cttcgtcgag    2220
tacttcagat cggctacacc ggagaccgag tacgggagga tgaacatcgg cagccggcca    2280
gccaagagga ggcccggcgg cggcatcacg accctgcgcg ccatcccctg gatcttctcg    2340
tggacccaga ccaggttcca cctccccgtg tggctgggag tcggcgccgc attcaagttc    2400
gccatcgaca aggacgtcag gaacttccag gtcctcaaag agatgtacaa cgagtggcca    2460
ttcttcaggg tcaccctgga cctgctggag atggttttcg ccaagggaga ccccggcatt    2520
gccggcttgt atgacgagct gcttgtggcg gaagaactca agcccttttgg gaagcagctc    2580 agggacaaat acgtggagac acagcagctt ctcctccaga tcgctgggca caaggatatt    2640
cttgaaggcg atccattcct gaagcagggg ctggtgctgc gcaacccta catcaccacc    2700 ctgaacgtgt tccaggccta cacgctgaag cggataaggg accccaactt caaggtgacg    2760
ccccagccgc cgctgtccaa ggagttcgcc gacgagaaca agcccgccgg actggtcaag    2820
ctgaacccgg cgagcgagta cccgcccggc ctggaagaca cgctcatcct caccatgaag    2880
ggcatcgccg ccggcatgca gaacactggc tag                                 2913

<210> SEQ ID NO 4
<211> LENGTH: 538
<212> TYPE: DNA
<213> ORGANISM: Artificial Sequence
<220> FEATURE:
<223> OTHER INFORMATION: CaMV 35S promoter sequence

<400> SEQUENCE: 4
catggagtca aagattcaaa tagaggacct aacagaactc gccgtaaaga ctggcgaaca     60
gttcatacag agtctcttac gactcaatga caagaagaaa atcttcgtca acatggtgga    120
gcacgacaca cttgtctact ccaaaaatat caaagataca gtctcagaag accaaagggc    180
aattgagact tttcaacaaa gggtaatatc cggaaacctc ctcggattcc attgcccagc    240
tatctgtcac tttattgtga agatagtgga aaggaaggt ggctcctaca atgccatca     300 ttgcgataaa ggaaaggcca tcgttgaaga tgcctctgcc gacagtggtc ccaaagatgg    360
acccccaccc acgaggagca tcgtggaaaa agaagacgtt ccaaccacgt cttcaaagca    420
agtggattga tgtgatatct ccactgacgt aagggatgac gcacaatccc actatccttc    480
gcaagaccct tcctctatat aaggaagttc atttcatttg gagagaacac gggggact     538

<210> SEQ ID NO 5
<211> LENGTH: 253
<212> TYPE: DNA
<213> ORGANISM: Artificial Sequence
<220> FEATURE:
<223> OTHER INFORMATION: nos (nopaline synthase) 3' UTR (polyA signal)

<400> SEQUENCE: 5
cgttcaaaca tttggcaata aagtttctta agattgaatc ctgttgccgg tcttgcgatg     60
attatcatat aatttctgtt gaattacgtt aagcatgtaa taattaacat gtaatgcatg    120
acgttattta tgagatgggt ttttatgatt agagtcccgc aattatacat ttaatacgcg    180
atagaaaaca aaatatagcg cgcaaactag gataaattat cgcgcgcggt gtcatctatg    240
ttactagatc ggg                                                       253
```

<210> SEQ ID NO 6
<211> LENGTH: 1026
<212> TYPE: DNA
<213> ORGANISM: Artificial Sequence
<220> FEATURE:
<223> OTHER INFORMATION: hygromycin phosphotransferase coding sequence

<400> SEQUENCE: 6

| | | | | | |
|---|---|---|---|---|---|
| ctatttctttt | gccctcggac | gagtgctggg | gcgtcggttt | ccactatcgg | cgagtacttc | 60 |
| tacacagcca | tcggtccaga | cggccgcgct | tctgcgggcg | atttgtgtac | gcccgacagt | 120 |
| cccggctccg | gatcggacga | ttgcgtcgca | tcgaccctgc | gcccaagctg | catcatcgaa | 180 |
| attgccgtca | accaagctct | gatagagttg | gtcaagacca | atgcggagca | tatacgcccg | 240 |
| gagtcgtggc | gatcctgcaa | gctccggatg | cctccgctcg | aagtagcgcg | tctgctgctc | 300 |
| catacaagcc | aaccacggcc | tccagaagaa | gatgttggcg | acctcgtatt | gggaatcccc | 360 |
| gaacatcgcc | tcgctccagt | caatgaccgc | tgttatgcgg | ccattgtccg | tcaggacatt | 420 |
| gttggagccg | aaatccgcgt | gcacgaggtg | ccggacttcg | gggcagtcct | cggcccaaag | 480 |
| catcagctca | tcgagagcct | gcgcgacgga | cgcactgacg | gtgtcgtcca | tcacagtttg | 540 |
| ccagtgatac | acatggggat | cagcaatcgc | gcatatgaaa | tcacgccatg | tagtgtattg | 600 |
| accgattcct | tgcggtccga | atgggccgaa | cccgctcgtc | tggctaagat | cggccgcagc | 660 |
| gatcgcatcc | atagcctccg | cgaccggttg | tagaacagcg | ggcagttcgg | tttcaggcag | 720 |
| gtcttgcaac | gtgacaccct | gtgcacggcg | ggagatgcaa | taggtcaggc | tctcgctaaa | 780 |
| ctccccaatg | tcaagcactt | ccggaatcgg | gagcgcggcc | gatgcaaagt | gccgataaac | 840 |
| ataacgatct | ttgtagaaac | catcggcgca | gctatttacc | cgcaggacat | atccacgccc | 900 |
| tcctacatcg | aagctgaaag | cacgagattc | ttcgccctcc | gagagctgca | tcaggtcgga | 960 |
| gacgctgtcg | aacttttcga | tcagaaactt | ctcgacagac | gtcgcggtga | gttcaggctt | 1020 |
| tttcat | | | | | 1026 |

<210> SEQ ID NO 7
<211> LENGTH: 7955
<212> TYPE: DNA
<213> ORGANISM: Artificial Sequence
<220> FEATURE:
<223> OTHER INFORMATION: Expression construct for coexpression of AspAT,
     GS, and PEPCase

<400> SEQUENCE: 7

| | | | | | |
|---|---|---|---|---|---|
| catggagtca | agattcaaa | tagaggacct | aacagaactc | gccgtaaaga | ctggcgaaca | 60 |
| gttcatacag | agtctcttac | gactcaatga | caagaagaaa | atcttcgtca | acatggtgga | 120 |
| gcacgacaca | cttgtctact | ccaaaaatat | caaagataca | gtctcagaag | accaaagggc | 180 |
| aattgagact | tttcaacaaa | gggtaatatc | cggaaacctc | ctcggattcc | attgcccagc | 240 |
| tatctgtcac | tttattgtga | agatagtgga | aaaggaaggt | ggctcctaca | aatgccatca | 300 |
| ttgcgataaa | ggaaaggcca | tcgttgaaga | tgcctctgcc | gacagtggtc | ccaaagatgg | 360 |
| acccccaccc | acgaggagca | tcgtggaaaa | agaagacgtt | ccaaccacgt | cttcaaagca | 420 |
| agtggattga | tgtgatatct | ccactgacgt | aagggatgac | gcacaatccc | actatccttc | 480 |
| gcaagaccct | tcctctatat | aaggaagttc | atttcatttg | gagagaacac | ggggggactct | 540 |
| tgaccatggt | agatcttatg | gcttctcacg | acagcatcc | cgcttctcca | acctccgctt | 600 |
| ctgattccgt | cttcaatcac | ctcgttcgtg | ctcccgaaga | tcctatcctc | ggggtaactg | 660 |
| tcgcttataa | caaagatcca | agtccagtta | agctcaactt | gggagttggt | gcttaccgaa | 720 |

-continued

```
ctgaggaagg aaaacctctt gttttgaatg tagtgaggcg agttgaacag caactcataa     780
atgacgtgtc acgcaacaag gaatatattc cgatcgttgg gcttgctgat tttaataaat     840
tgagtgctaa gcttattttt ggggctgaca gccctgctat tcaagacaac agggttacca     900
ctgttcaatg cttgtctgga actggttctt taagagttgg gggtgaattt ttggctaaac     960
actatcacca acggactata tacttgccaa caccaacttg gggcaatcac ccgaaggttt    1020
tcaacttagc aggcttgtct gtcaaaacat accgctacta tgctccagca acacgaggac    1080
ttgactttca aggacttctg gaagaccttg gttctgctcc atctggatct attgttttgc    1140
tacatgcatg cgcacataac cccactggtg tggatccaac ccttgagcaa tgggagcaga    1200
ttaggcagct aataagatca aaagctttgt tacctttctt tgacagtgct tatcagggtt    1260
ttgctagtgg aagtctagat gcagatgccc aacctgttcg tttgtttgtt gctgatggag    1320
gcgaattgct ggtagcacaa agctatgcaa agaatctggg tctttatggg gaacgtgttg    1380
gcgccttaag cattgtctgc aagtcagctg atgttgcaag cagggttgag agccagctga    1440
agctagtgat taggcccatg tactcaagtc ctcccattca tggtgcatcc attgtggctg    1500
ccattctcaa ggaccggaat tgttcaatg actggactat tgagttgaag gcaatggctg    1560
atcgcatcat cagtatgcgc caagaacttt tcgatgcttt atgttccaga ggcacacctg    1620
gcgattggag tcacattatc aaacagattg gaatgtttac tttcactgga ttgaatgcgg    1680
aacaagtttc cttcatgact aaagagttcc atatatacat gacatctgat gggaggatta    1740
gcatggctgg tctgagttcc aaaactgtcc cacttctggc ggatgcgata catgcagctg    1800
taacccgagt tgtctaacac gtgtgaattg gtgaccagct cgaatttccc cgatcgttca    1860
aacatttggc aataaagttt cttaagattg aatcctgttg ccggtcttgc gatgattatc    1920
atataatttc tgttgaatta cgttaagcat gtaataatta acatgtaatg catgacgtta    1980
tttatgagat gggtttttat gattagagtc ccgcaattat acatttaata cgcgatagaa    2040
aacaaaatat agcgcgcaaa ctaggataaa ttatcgcgcg cggtgtcatc tatgttacta    2100
gatcgggaat taaactagta atggcgaatg ctagagcagc ttgagcttgg atcagattgt    2160
cgtttcccgc cttcagttta gcttcatgga gtcaaagatt caaatagagg acctaacaga    2220
actcgccgta aagactggcg aacagttcat acagagtctc ttacgactca atgacaagaa    2280
gaaaatcttc gtcaacatgg tggagcacga cacacttgtc tactccaaaa atatcaaaga    2340
tacagtctca gaagaccaaa gggcaattga acttttcaa caagggtaa tatccggaaa    2400
cctcctcgga ttccattgcc cagctatctg tcactttatt gtgaagatag tggaaaagga    2460
aggtggctcc tacaaatgcc atcattgcga taaaggaaag gccatcgttg aagatgcctc    2520
tgccgacagt ggtcccaaag atggacccc  acccacgagg agcatcgtgg aaaaagaaga    2580
cgttccaacc acgtcttcaa agcaagtgga ttgatgtgat atctccactg acgtaaggga    2640
tgacgcacaa tcccactatc cttcgcaaga cccttcctct atataaggaa gttcatttca    2700
tttggagaga acacggggga ctcttgacca tggctcatct ttcagatctc gttaatctca    2760
atctctctga ctccactcag aaaattattg ctgaatacat atggattggt ggatcaggaa    2820
tggacgtcag gagcaaagcc agaacacttt ctggacctgt tgatgatcct tcaaagcttc    2880
ccaaatggaa ttatgatggt tctagcacag acaagctcc tggagaagac agtgaagaga    2940
tcctatatcc tcaagcaatt ttcaaggatc cattcagaag gggcaacaat atcttggtca    3000
tttgtgattg ttacacccca gctggtgaac ccattccaac aaacaaaagg cacagtgctg    3060
ccaagatttt cagccaccct gatgttgttg ttgaggaacc ctggtatggt cttgagcaag    3120
```

-continued

```
aatacacctt gttgcaaaaa gatatcaatt ggcctcttgg atggcctctt ggtggttttc     3180
ctggaccaca gggaccatac tattgcggaa ttggagctgg aaaggtcttt ggacgcgata     3240
tcgttgactc tcattataag gcatgtctct atgctgggat aacatcagt ggtatcaatg      3300
gagaagtgat gcccggacag tgggaatttc aagttggacc ttcagttggc atttcagcag    3360
ctgatgaatt gtgggcagct cgttacattc ttgagaggat tactgagatt gctggagttg    3420
tggtctcatt tgaccccaaa cctattccgg gtgactggaa tggtgctgga gctcacacaa    3480
actacagcac aaagtctatg aggaatgaag gaggctatga agtcattaag aaggcaattg    3540
agaaccttgg actgaggcac aaggagcata ttgcagcata tggtgaaggc aacgagcgtc    3600
gtctcactgg aagacacgaa acagctgaca tcaacacatt caaatgggga gttgcgaacc    3660
gtggtgcatc tattcgtgtg gaagagaca cggagagaga agggaaggga tacttcgagg     3720
ataggaggcc tgcttcgaat atggatccat tcgtcgtgac ttccatgatt gctgagacca    3780
ctatcctatc cgagccttga ggtcaccagc tcgaatttcc ccgatcgttc aaacatttgg    3840
caataaagtt tcttaagatt gaatcctgtt gccggtcttg cgatgattat catataattt    3900
ctgttgaatt acgttaagca tgtaataatt aacatgtaat gcatgacgtt atttatgaga    3960
tgggttttta tgattagagt cccgcaatta tacatttaat acgcgataga aaacaaaata    4020
tagcgcgcaa actaggataa attatcgcgc gcggtgtcat ctatgttact agatcgggaa    4080
ttaaactatc agtgtttgac aggatatatt ggcgggcgcg ccaatggcga atgctagagc    4140
agcttgagct tggatcagat tgtcgtttcc cgccttcagt ttagcttcat ggagtcaaag    4200
attcaaatag aggacctaac agaactcgcc gtaaagactg gcgaacagtt catacagagt    4260
ctcttacgac tcaatgacaa gaagaaaatc ttcgtcaaca tggtggagca cgacacactt    4320
gtctactcca aaaatatcaa agatacagtc tcagaagacc aaagggcaat tgagactttt    4380
caacaagggg taatatccgg aaacctcctc ggattccatt gcccagctat ctgtcacttt    4440
attgtgaaga tagtggaaaa ggaaggtggc tcctacaaat gccatcattg cgataaagga    4500
aaggccatcg ttgaagatgc ctctgccgac agtggtccca agatggaccc cccacccacg    4560
aggagcatcg tggaaaaaga agacgttcca accacgtctt caaagcaagt ggattgatgt    4620
gatatctcca ctgacgtaag ggatgacgca caatcccact atccttcgca agacccttcc    4680
tctatataag gaagttcatt tcatttggag agaacacggg ggactcttga ccatggtaga    4740
tcttatggcg tcgaccaagg ctcccggccc cggcgagaag caccactcca tcgacgcgca    4800
gctccgtcag ctggtcccag gcaaggtctc cgaggacgac aagctcatcg agtacgatgc    4860
gctgctcgtc gaccgcttcc tcaacatcct ccaggacctc cacgggccca gccttcgcga    4920
atttgtccag gagtgctacg aggtctcagc cgactacgag ggcaaaggag acacgacgaa    4980
gctgggcgag ctcggcgcca agctcacggg gctggccccc gccgacgcca tcctcgtggc    5040
gagctccatc ctgcacatgc tcaacctcgc caacctggcc gaggaggtgc agatcgcgca    5100
ccgccgccgc aacagcaagc tcaagaaagg tgggttcgcc gacgagggct ccgccaccac    5160
cgagtccgac atcgaggaga cgctcaagcg cctcgtgtcc gaggtcggca gtcccccga    5220
ggaggtgttc gaggcgctca gaaccagac cgtcgacctc gtcttcaccg cgcatcctac    5280
gcagtccgcc cgccgctcgc tcctgcaaaa aaatgccagg atccgaaatt gtctgaccca    5340
gctgaatgcc aaggacatca ctgacgacga caagcaggag ctcgatgagg ctctgcagag    5400
agagatccaa gcagccttca gaaccgatga atcaggagg gcacaaccca ccccgcaggc    5460
cgaaatgcgc tatgggatga gctacatcca tgagactgta tggaagggtg tgcctaagtt    5520
```

```
cttgcgccgt gtggatacag ccctgaagaa tatcggcatc aatgagcgcc ttccctacaa   5580
tgtttctctc attcggttct cttcttggat gggtggtgac cgcgatggaa atccaagagt   5640
taccccggag gtgacaagag atgtatgctt gctggccaga atgatggctg caaacttgta   5700
catcgatcag attgaagagc tgatgtttga gctctctatg tggcgctgca acgatgagct   5760
tcgtgttcgt gccgaagagc tccacagttc gtctggttcc aaagttacca agtattacat   5820
agaattctgg aagcaaattc ctccaaacga gccctaccgg gtgatactag gccatgtaag   5880
ggacaagctg tacaacacac gcgagcgtgc tcgccatctg ctggcttctg agtttctga   5940 aatttcagcg gaatcgtcat ttaccagtat cgaagagttc cttgagccac ttgagctgtg   6000
ctacaaatca ctgtgtgact gcggcgacaa ggccatcgcg gacgggagcc tcctggacct   6060
cctgcgccag gtgttcacgt cgggctctc cctggtgaag ctggacatcc ggcaggagtc   6120
ggagcggcac accgacgtga tcgacgccat caccacgcac ctcggcatcg ggtcgtaccg   6180
cgagtggccc gaggacaaga ggcaggagtg gctgctgtcg gagctgcgag gcaagcgccc   6240
gctgctgccc ccggaccttc cccagaccga cgagatcgcc gacgtcatcg gcgcgttcca   6300
cgtcctcgcg gagctcccgc ccgacagctt cggcccctac atcatctcca tggcgacggc   6360
cccctcggac gtgctcgccg tggagctcct gcagcgcgag tgcggcgtgc gccagccgct   6420
gcccgtggtg ccgctgttcg agaggctggc cgacctgcag tcggcgcccg cgtccgtgga   6480
gcgcctcttc tcggtggact ggtacatgga ccggatcaag ggcaagcagc aggtcatggt   6540
cggctactcc gactccggca aggacgccgg ccgcctgtcc gcggcgtggc agctgtacag   6600
ggcgcaggag gagatggcgc aggtggccaa gcgctacggc gtcaagctca ccttgttcca   6660
cggccgcgga ggcaccgtgg gcaggggtgg cgggcccacg caccttgcca tcctgtccca   6720
gccgccggac accatcaacg ggtccatccg tgtgacggtg cagggcgagg tcatcgagtt   6780
ctgcttcggg gaggagcacc tgtgcttcca gactctgcag cgcttcacgg ccgccacgct   6840
ggagcacggc atgcacccgc cggtctctcc caagcccgag tggcgcaagc tcatggacga   6900
gatggcggtc gtggccacgg aggagtaccg ctccgtcgtc gtcaaggagg cgcgcttcgt   6960
cgagtacttc agatcggcta caccggagac cgagtacggg aggatgaaca tcggcagccg   7020
gccagccaag aggaggcccg gcggcggcat cacgaccctg cgccgccatcc cctggatctt   7080 ctcgtggacc cagaccaggt tccacctccc cgtgtggctg ggagtcggcg ccgcattcaa   7140
gttcgccatc gacaaggacg tcaggaactt ccaggtcctc aaagagatgt acaacgagtg   7200
gccattcttc agggtcaccc tggacctgct ggagatggtt ttcgccaagg gagacccgg   7260 cattgccggc ttgtatgacg agctgcttgt ggcggaagaa ctcaagccct ttgggaagca   7320
gctcagggac aaatacgtgg agacacagca gcttctcctc cagatcgctg gcacaagga   7380 tattcttgaa ggcgatccat tcctgaagca ggggctggtg ctgcgcaacc cctacatcac   7440
caccctgaac gtgttccagg cctacacgct gaagcggata agggacccca acttcaaggt   7500 gacgcccag ccgccgctgt ccaaggagtt cgccgacgag aacaagcccg ccggactggt   7560
caagctgaac ccggcgagcg agtacccgcc cggcctggaa gacacgctca tcctcaccat   7620
gaagggcatc gccgccggca tgcagaacac tggctaggct gaggacacgt gtgaattggt   7680
gaccagctcg aatttccccg atcgttcaaa catttggcaa taaagtttct taagattgaa   7740
tcctgttgcc ggtcttgcga tgattatcat ataatttctg ttgaattacg ttaagcatgt   7800
aataattaac atgtaatgca tgacgttatt tatgagatgg gtttttatga ttagagtccc   7860
```

```
gcaattatac atttaatacg cgatagaaaa caaaatatag cgcgcaaact aggataaatt      7920
atcgcgcgcg gtgtcatcta tgttactaga tcggg                                7955
```

<210> SEQ ID NO 8
<211> LENGTH: 28
<212> TYPE: DNA
<213> ORGANISM: Artificial Sequence
<220> FEATURE:
<223> OTHER INFORMATION: Forward primer for amplification of N. tabacum
      GS, including restriction site for NcoI

<400> SEQUENCE: 8

```
tgccatggct catctttcgg atctcgtt                                           28
```

<210> SEQ ID NO 9
<211> LENGTH: 30
<212> TYPE: DNA
<213> ORGANISM: Artificial Sequence
<220> FEATURE:
<223> OTHER INFORMATION: Reverse primer for amplification of N. tabacum
      GS, including restriction site for BstEII

<400> SEQUENCE: 9

```
gggtgacctc aaggctcgga taggatagtg                                         30
```

<210> SEQ ID NO 10
<211> LENGTH: 32
<212> TYPE: DNA
<213> ORGANISM: Artificial Sequence
<220> FEATURE:
<223> OTHER INFORMATION: Forward primer for amplification of Soybean
      AspAT, including restriction site for BglII

<400> SEQUENCE: 10

```
catagatctt atggcttctc acgacagcat ct                                      32
```

<210> SEQ ID NO 11
<211> LENGTH: 31
<212> TYPE: DNA
<213> ORGANISM: Artificial Sequence
<220> FEATURE:
<223> OTHER INFORMATION: Reverse primer for amplification of Soybean
      AspAT, including restriction site for PmlI

<400> SEQUENCE: 11

```
gccacgtgtt agacaactcg ggttacagct g                                       31
```

<210> SEQ ID NO 12
<211> LENGTH: 30
<212> TYPE: DNA
<213> ORGANISM: Artificial Sequence
<220> FEATURE:
<223> OTHER INFORMATION: Forward primer for amplification of Zea mays
      PEPCase, including restriction site for BglII

<400> SEQUENCE: 12

```
atagatctta tggcgtcgac caaggctccg                                         30
```

<210> SEQ ID NO 13
<211> LENGTH: 31
<212> TYPE: DNA
<213> ORGANISM: Artificial Sequence
<220> FEATURE:
<223> OTHER INFORMATION: Reverse primer for amplification of Zea mays
      PEPCase, including restriction site for SpeI

<400> SEQUENCE: 13
agactagtgc cagtgttctg catgccggcg g                            31

<210> SEQ ID NO 14
<211> LENGTH: 34
<212> TYPE: DNA
<213> ORGANISM: Artificial Sequence
<220> FEATURE:
<223> OTHER INFORMATION: Forward primer for amplification of CaMV 35S
      promoter, including restriction site for SpeI

<400> SEQUENCE: 14
ggactagtaa tggcgaatgc tagagcagct tgag                         34

<210> SEQ ID NO 15
<211> LENGTH: 55
<212> TYPE: DNA
<213> ORGANISM: Artificial Sequence
<220> FEATURE:
<223> OTHER INFORMATION: Reverse primer for amplification of Nos
      terminator sequence, including restriction sites for AscI, BbvCI,
      PmlI

<400> SEQUENCE: 15
gccacgtgtc ctcagctggc gcgcccgcca atatatcctg tcaaacactg atagt   55

<210> SEQ ID NO 16
<211> LENGTH: 35
<212> TYPE: DNA
<213> ORGANISM: Artificial Sequence
<220> FEATURE:
<223> OTHER INFORMATION: Reverse primer for amplification of Nos
      terminator sequence, including restriction site for SpeI

<400> SEQUENCE: 16
ggactagttt aattcccgat ctagtaacat agatg                        35

<210> SEQ ID NO 17
<211> LENGTH: 38
<212> TYPE: DNA
<213> ORGANISM: Artificial Sequence
<220> FEATURE:
<223> OTHER INFORMATION: Forward primer for amplification of CaMV 35S
      promoter, including restriction site for AscI

<400> SEQUENCE: 17
atctggcgcg ccaatggcga atgctagagc agcttgag                     38

<210> SEQ ID NO 18
<211> LENGTH: 33
<212> TYPE: DNA
<213> ORGANISM: Artificial Sequence
<220> FEATURE:
<223> OTHER INFORMATION: Reverse primer for amplification of Zea mays
      PEPCase, including restriction site for BbvCI

<400> SEQUENCE: 18
gtgcctcagc ctagccagtg ttctgcatgc cgg                          33

<210> SEQ ID NO 19
<211> LENGTH: 20
<212> TYPE: DNA
<213> ORGANISM: Artificial Sequence
<220> FEATURE:
<223> OTHER INFORMATION: Forward primer for amplification of hygromycin
      phosphotransferase

<400> SEQUENCE: 19
gagggcgaag aatctcgtgc                                         20

<210> SEQ ID NO 20
<211> LENGTH: 22
<212> TYPE: DNA
<213> ORGANISM: Artificial Sequence
<220> FEATURE:
<223> OTHER INFORMATION: Reverse primer for amplification of hygromycin
      phosphotransferase

<400> SEQUENCE: 20
gatgttggcg acctcgtatt gg                                      22

<210> SEQ ID NO 21
<211> LENGTH: 20
<212> TYPE: DNA
<213> ORGANISM: Artificial Sequence
<220> FEATURE:
<223> OTHER INFORMATION: Forward primer for RT-PCR evaluation of Zea
      mays PEPCase transgene Expression

<400> SEQUENCE: 21
acgtcaggaa cttccaggtc                                         20

<210> SEQ ID NO 22
<211> LENGTH: 19
<212> TYPE: DNA
<213> ORGANISM: Artificial Sequence
<220> FEATURE:
<223> OTHER INFORMATION: Reverse primer for RT-PCR evaluation of Zea
      mays PEPCase transgene expression

<400> SEQUENCE: 22
cttgttctcg tcggcgaac                                          19

<210> SEQ ID NO 23
<211> LENGTH: 19
<212> TYPE: DNA
<213> ORGANISM: Artificial Sequence
<220> FEATURE:
<223> OTHER INFORMATION: Forward primer for RT-PCR evaluation of
      Nicotiana tabacum GS transgene expression

<400> SEQUENCE: 23
actttctgga cctgttgat                                          19

<210> SEQ ID NO 24
<211> LENGTH: 16
<212> TYPE: DNA
<213> ORGANISM: Artificial Sequence
<220> FEATURE:
<223> OTHER INFORMATION: Reverse primer for RT-PCR evaluation of
      Nicotiana tabacum GS transgene expression

<400> SEQUENCE: 24
ggcagcactg tgcctt                                             16

<210> SEQ ID NO 25
<211> LENGTH: 21
<212> TYPE: DNA
<213> ORGANISM: Artificial Sequence
<220> FEATURE:
<223> OTHER INFORMATION: Forward primer for RT-PCR evaluation of
      Soybean AspAT transgene expression

```
<400> SEQUENCE: 25
atggcttctc acgacagcat c                                              21

<210> SEQ ID NO 26
<211> LENGTH: 24
<212> TYPE: DNA
<213> ORGANISM: Artificial Sequence
<220> FEATURE:
<223> OTHER INFORMATION: Reverse primer for RT-PCR evaluation of Soybean
      AspAT transgene expression

<400> SEQUENCE: 26
ttgcgtgaca cgtcatttat gagt                                           24

<210> SEQ ID NO 27
<211> LENGTH: 22
<212> TYPE: DNA
<213> ORGANISM: Artificial Sequence
<220> FEATURE:
<223> OTHER INFORMATION: Forward primer for RT-PCR evaluation of 26S
      rRNA

<400> SEQUENCE: 27
cacaatgata ggaagagccg ac                                             22

<210> SEQ ID NO 28
<211> LENGTH: 24
<212> TYPE: DNA
<213> ORGANISM: Artificial Sequence
<220> FEATURE:
<223> OTHER INFORMATION: Reverse primer for RT-PCR evaluation of 26S
      rRNA

<400> SEQUENCE: 28
caagggaacg ggcttggcag aatc                                           24

<210> SEQ ID NO 29
<211> LENGTH: 419
<212> TYPE: PRT
<213> ORGANISM: Glycine max

<400> SEQUENCE: 29
```

Met Ala Ser His Asp Ser Ile Ser Ala Ser Pro Thr Ser Ala Ser Asp
1               5                   10                  15

Ser Val Phe Asn His Leu Val Arg Ala Pro Glu Asp Pro Ile Leu Gly
            20                  25                  30

Val Thr Val Ala Tyr Asn Lys Asp Pro Ser Pro Val Lys Leu Asn Leu
        35                  40                  45

Gly Val Gly Ala Tyr Arg Thr Glu Glu Gly Lys Pro Leu Val Leu Asn
    50                  55                  60

Val Val Arg Arg Val Glu Gln Gln Leu Ile Asn Asp Val Ser Arg Asn
65                  70                  75                  80

Lys Glu Tyr Ile Pro Ile Val Gly Leu Ala Asp Phe Asn Lys Leu Ser
                85                  90                  95

Ala Lys Leu Ile Phe Gly Ala Asp Ser Pro Ala Ile Gln Asp Asn Arg
            100                 105                 110

Val Thr Thr Val Gln Cys Leu Ser Gly Thr Gly Ser Leu Arg Val Gly
        115                 120                 125

Gly Glu Phe Leu Ala Lys His Tyr His Gln Arg Thr Ile Tyr Leu Pro
    130                 135                 140

```
Thr Pro Thr Trp Gly Asn His Pro Lys Val Phe Asn Leu Ala Gly Leu
145                 150                 155                 160

Ser Val Lys Thr Tyr Arg Tyr Tyr Ala Pro Ala Thr Arg Gly Leu Asp
                165                 170                 175

Phe Gln Gly Leu Leu Glu Asp Leu Gly Ser Ala Pro Ser Gly Ser Ile
            180                 185                 190

Val Leu Leu His Ala Cys Ala His Asn Pro Thr Gly Val Asp Pro Thr
            195                 200                 205

Leu Glu Gln Trp Glu Gln Ile Arg Gln Leu Ile Arg Ser Lys Ala Leu
210                 215                 220

Leu Pro Phe Phe Asp Ser Ala Tyr Gln Gly Phe Ala Ser Gly Ser Leu
225                 230                 235                 240

Asp Ala Asp Ala Gln Pro Val Arg Leu Phe Val Ala Asp Gly Gly Glu
                245                 250                 255

Leu Leu Val Ala Gln Ser Tyr Ala Lys Asn Leu Gly Leu Tyr Gly Glu
            260                 265                 270

Arg Val Gly Ala Leu Ser Ile Val Cys Lys Ser Ala Asp Val Ala Ser
            275                 280                 285

Arg Val Glu Ser Gln Leu Lys Leu Val Ile Arg Pro Met Tyr Ser Ser
290                 295                 300

Pro Pro Ile His Gly Ala Ser Ile Val Ala Ala Ile Leu Lys Asp Arg
305                 310                 315                 320

Asn Leu Phe Asn Asp Trp Thr Ile Glu Leu Lys Ala Met Ala Asp Arg
                325                 330                 335

Ile Ile Ser Met Arg Gln Glu Leu Phe Asp Ala Leu Cys Ser Arg Gly
            340                 345                 350

Thr Pro Gly Asp Trp Ser His Ile Ile Lys Gln Ile Gly Met Phe Thr
            355                 360                 365

Phe Thr Gly Leu Asn Ala Glu Gln Val Ser Phe Met Thr Lys Glu Phe
370                 375                 380

His Ile Tyr Met Thr Ser Asp Gly Arg Ile Ser Met Ala Gly Leu Ser
385                 390                 395                 400

Ser Lys Thr Val Pro Leu Leu Ala Asp Ala Ile His Ala Ala Val Thr
                405                 410                 415

Arg Val Val

<210> SEQ ID NO 30
<211> LENGTH: 356
<212> TYPE: PRT
<213> ORGANISM: Nicotiana tabacum

<400> SEQUENCE: 30

Met Ala His Leu Ser Asp Leu Val Asn Leu Asn Leu Ser Asp Ser Thr
1               5                   10                  15

Gln Lys Ile Ile Ala Glu Tyr Ile Trp Ile Gly Gly Ser Gly Met Asp
                20                  25                  30

Val Arg Ser Lys Ala Arg Thr Leu Ser Gly Pro Val Asp Asp Pro Ser
                35                  40                  45

Lys Leu Pro Lys Trp Asn Tyr Asp Gly Ser Ser Thr Gly Gln Ala Pro
            50                  55                  60

Gly Glu Asp Ser Glu Glu Ile Leu Tyr Pro Gln Ala Ile Phe Lys Asp
65                  70                  75                  80

Pro Phe Arg Arg Gly Asn Asn Ile Leu Val Ile Cys Asp Cys Tyr Thr
                85                  90                  95
```

-continued

```
Pro Ala Gly Glu Pro Ile Pro Thr Asn Lys Arg His Ser Ala Ala Lys
                100                 105                 110

Ile Phe Ser His Pro Asp Val Val Glu Pro Trp Tyr Gly Leu
        115                 120                 125

Glu Gln Glu Tyr Thr Leu Leu Gln Lys Asp Ile Asn Trp Pro Leu Gly
    130                 135                 140

Trp Pro Leu Gly Gly Phe Pro Gly Pro Gln Gly Pro Tyr Tyr Cys Gly
145                 150                 155                 160

Ile Gly Ala Gly Lys Val Phe Gly Arg Asp Ile Val Asp Ser His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Ala Asp Glu Leu Trp Ala Ala Arg Tyr Ile Leu Glu Arg Ile
    210                 215                 220

Thr Glu Ile Ala Gly Val Val Ser Phe Asp Pro Lys Pro Ile Pro
225                 230                 235                 240

Gly Asp Trp Asn Gly Ala Gly Ala His Thr Asn Tyr Ser Thr Lys Ser
                245                 250                 255

Met Arg Asn Glu Gly Gly Tyr Glu Val Ile Lys Lys Ala Ile Glu Asn
            260                 265                 270

Leu Gly Leu Arg His Lys Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Lys Trp Gly Val Ala Asn Arg Gly Ala Ser Ile Arg Val Gly Arg Asp
305                 310                 315                 320

Thr Glu Arg Glu Gly Lys Gly Tyr Phe Glu Asp Arg Arg Pro Ala Ser
                325                 330                 335

Asn Met Asp Pro Phe Val Val Thr Ser Met Ile Ala Glu Thr Thr Ile
            340                 345                 350

Leu Ser Glu Pro
        355

<210> SEQ ID NO 31
<211> LENGTH: 970
<212> TYPE: PRT
<213> ORGANISM: Zea mays

<400> SEQUENCE: 31

Met Ala Ser Thr Lys Ala Pro Gly Pro Gly Glu Lys His His Ser Ile
1               5                   10                  15

Asp Ala Gln Leu Arg Gln Leu Val Pro Gly Lys Val Ser Glu Asp Asp
                20                  25                  30

Lys Leu Ile Glu Tyr Asp Ala Leu Leu Val Asp Arg Phe Leu Asn Ile
            35                  40                  45

Leu Gln Asp Leu His Gly Pro Ser Leu Arg Glu Phe Val Gln Glu Cys
        50                  55                  60

Tyr Glu Val Ser Ala Asp Tyr Glu Gly Lys Gly Asp Thr Thr Lys Leu
65                  70                  75                  80

Gly Glu Leu Gly Ala Lys Leu Thr Gly Leu Ala Pro Ala Asp Ala Ile
                85                  90                  95

Leu Val Ala Ser Ser Ile Leu His Met Leu Asn Leu Ala Asn Leu Ala
            100                 105                 110
```

-continued

Glu Glu Val Gln Ile Ala His Arg Arg Asn Ser Lys Leu Lys Lys
            115                 120                 125

Gly Gly Phe Ala Asp Glu Gly Ser Ala Thr Thr Glu Ser Asp Ile Glu
130                 135                 140

Glu Thr Leu Lys Arg Leu Val Ser Glu Val Gly Lys Ser Pro Glu Glu
145                 150                 155                 160

Val Phe Glu Ala Leu Lys Asn Gln Thr Val Asp Leu Val Phe Thr Ala
                165                 170                 175

His Pro Thr Gln Ser Ala Arg Arg Ser Leu Leu Gln Lys Asn Ala Arg
            180                 185                 190

Ile Arg Asn Cys Leu Thr Gln Leu Asn Ala Lys Asp Ile Thr Asp Asp
        195                 200                 205

Asp Lys Gln Glu Leu Asp Glu Ala Leu Gln Arg Glu Ile Gln Ala Ala
    210                 215                 220

Phe Arg Thr Asp Glu Ile Arg Arg Ala Gln Pro Thr Pro Gln Ala Glu
225                 230                 235                 240

Met Arg Tyr Gly Met Ser Tyr Ile His Glu Thr Val Trp Lys Gly Val
                245                 250                 255

Pro Lys Phe Leu Arg Arg Val Asp Thr Ala Leu Lys Asn Ile Gly Ile
            260                 265                 270

Asn Glu Arg Leu Pro Tyr Asn Val Ser Leu Ile Arg Phe Ser Ser Trp
        275                 280                 285

Met Gly Gly Asp Arg Asp Gly Asn Pro Arg Val Thr Pro Glu Val Thr
    290                 295                 300

Arg Asp Val Cys Leu Leu Ala Arg Met Met Ala Ala Asn Leu Tyr Ile
305                 310                 315                 320

Asp Gln Ile Glu Glu Leu Met Phe Glu Leu Ser Met Trp Arg Cys Asn
                325                 330                 335

Asp Glu Leu Arg Val Arg Ala Glu Glu Leu His Ser Ser Ser Gly Ser
            340                 345                 350

Lys Val Thr Lys Tyr Tyr Ile Glu Phe Trp Lys Gln Ile Pro Pro Asn
        355                 360                 365

Glu Pro Tyr Arg Val Ile Leu Gly His Val Arg Asp Lys Leu Tyr Asn
    370                 375                 380

Thr Arg Glu Arg Ala Arg His Leu Leu Ala Ser Gly Val Ser Glu Ile
385                 390                 395                 400

Ser Ala Glu Ser Ser Phe Thr Ser Ile Glu Glu Phe Leu Glu Pro Leu
                405                 410                 415

Glu Leu Cys Tyr Lys Ser Leu Cys Asp Cys Gly Asp Lys Ala Ile Ala
            420                 425                 430

Asp Gly Ser Leu Leu Asp Leu Arg Gln Val Phe Thr Phe Gly Leu
        435                 440                 445

Ser Leu Val Lys Leu Asp Ile Arg Gln Glu Ser Glu Arg His Thr Asp
    450                 455                 460

Val Ile Asp Ala Ile Thr Thr His Leu Gly Ile Gly Ser Tyr Arg Glu
465                 470                 475                 480

Trp Pro Glu Asp Lys Arg Gln Glu Trp Leu Leu Ser Glu Leu Arg Gly
                485                 490                 495

Lys Arg Pro Leu Leu Pro Pro Asp Leu Pro Gln Thr Asp Glu Ile Ala
            500                 505                 510

Asp Val Ile Gly Ala Phe His Val Leu Ala Glu Leu Pro Pro Asp Ser
        515                 520                 525

```
Phe Gly Pro Tyr Ile Ile Ser Met Ala Thr Ala Pro Ser Asp Val Leu
    530                 535                 540

Ala Val Glu Leu Leu Gln Arg Glu Cys Gly Val Arg Gln Pro Leu Pro
545                 550                 555                 560

Val Val Pro Leu Phe Glu Arg Leu Ala Asp Leu Gln Ser Ala Pro Ala
                565                 570                 575

Ser Val Glu Arg Leu Phe Ser Val Asp Trp Tyr Met Asp Arg Ile Lys
            580                 585                 590

Gly Lys Gln Gln Val Met Val Gly Tyr Ser Asp Ser Lys Asp Ala
        595                 600                 605

Gly Arg Leu Ser Ala Ala Trp Gln Leu Tyr Arg Ala Gln Glu Glu Met
    610                 615                 620

Ala Gln Val Ala Lys Arg Tyr Gly Val Lys Leu Thr Leu Phe His Gly
625                 630                 635                 640

Arg Gly Gly Thr Val Gly Arg Gly Gly Pro Thr His Leu Ala Ile
                645                 650                 655

Leu Ser Gln Pro Pro Asp Thr Ile Asn Gly Ser Ile Arg Val Thr Val
            660                 665                 670

Gln Gly Glu Val Ile Glu Phe Cys Phe Gly Glu His Leu Cys Phe
        675                 680                 685

Gln Thr Leu Gln Arg Phe Thr Ala Ala Thr Leu Glu His Gly Met His
    690                 695                 700

Pro Pro Val Ser Pro Lys Pro Glu Trp Arg Lys Leu Met Asp Glu Met
705                 710                 715                 720

Ala Val Val Ala Thr Glu Glu Tyr Arg Ser Val Val Lys Glu Ala
                725                 730                 735

Arg Phe Val Glu Tyr Phe Arg Ser Ala Thr Pro Glu Thr Glu Tyr Gly
            740                 745                 750

Arg Met Asn Ile Gly Ser Arg Pro Ala Lys Arg Pro Gly Gly Gly
        755                 760                 765

Ile Thr Thr Leu Arg Ala Ile Pro Trp Ile Phe Ser Trp Thr Gln Thr
    770                 775                 780

Arg Phe His Leu Pro Val Trp Leu Gly Val Gly Ala Ala Phe Lys Phe
785                 790                 795                 800

Ala Ile Asp Lys Asp Val Arg Asn Phe Gln Val Leu Lys Glu Met Tyr
                805                 810                 815

Asn Glu Trp Pro Phe Phe Arg Val Thr Leu Asp Leu Leu Glu Met Val
            820                 825                 830

Phe Ala Lys Gly Asp Pro Gly Ile Ala Gly Leu Tyr Asp Glu Leu Leu
        835                 840                 845

Val Ala Glu Glu Leu Lys Pro Phe Gly Lys Gln Leu Arg Asp Lys Tyr
    850                 855                 860

Val Glu Thr Gln Gln Leu Leu Leu Gln Ile Ala Gly His Lys Asp Ile
865                 870                 875                 880

Leu Glu Gly Asp Pro Phe Leu Lys Gln Gly Leu Val Leu Arg Asn Pro
                885                 890                 895

Tyr Ile Thr Thr Leu Asn Val Phe Gln Ala Tyr Thr Leu Lys Arg Ile
            900                 905                 910

Arg Asp Pro Asn Phe Lys Val Thr Pro Gln Pro Leu Ser Lys Glu
        915                 920                 925

Phe Ala Asp Glu Asn Lys Pro Ala Gly Leu Val Lys Leu Asn Pro Ala
    930                 935                 940
```

```
Ser Glu Tyr Pro Pro Gly Leu Glu Asp Thr Leu Ile Leu Thr Met Lys
945                 950                 955                 960

Gly Ile Ala Ala Gly Met Gln Asn Thr Gly
                965                 970
```